United States Patent
Mrva et al.

(10) Patent No.: US 7,343,202 B2
(45) Date of Patent: Mar. 11, 2008

(54) METHOD FOR AFFECTING URINARY FUNCTION WITH ELECTRODE IMPLANTATION IN ADIPOSE TISSUE

(75) Inventors: Joseph J. Mrva, Euclid, OH (US); Robert B. Strother, Willoughby Hills, OH (US); Geoffrey B. Thrope, Shaker Heights, OH (US); Julie Grill, Chapel Hill, NC (US); Maria Bennett, Lyndhurst, OH (US)

(73) Assignee: NDI Medical, LLC., Cleveland, OH (US)

( * ) Notice: Subject to any disclaimer, the term of this patent is extended or adjusted under 35 U.S.C. 154(b) by 0 days.

(21) Appl. No.: 11/150,419

(22) Filed: Jun. 10, 2005

(65) Prior Publication Data

US 2006/0004429 A1 Jan. 5, 2006

Related U.S. Application Data

(63) Continuation-in-part of application No. 10/777,771, filed on Feb. 12, 2004, now Pat. No. 7,120,499.

(60) Provisional application No. 60/578,742, filed on Jun. 10, 2004.

(51) Int. Cl.
*A61N 1/36* (2006.01)
(52) U.S. Cl. ............... 607/41; 607/40; 607/39; 607/116; 607/128; 607/143; 607/138
(58) Field of Classification Search .......... 607/39, 607/40–41, 116, 126, 128, 138, 143
See application file for complete search history.

(56) References Cited

U.S. PATENT DOCUMENTS

| | | |
|---|---|---|
| 3,727,616 A | 4/1973 | Lenzkes |
| 3,870,051 A | 3/1975 | Brindley |
| 3,939,843 A | 2/1976 | Smyth |
| 3,941,136 A | 3/1976 | Bucalo |
| 4,232,679 A | 11/1980 | Schulman |
| 4,262,678 A | 4/1981 | Stokes |
| 4,406,288 A | 9/1983 | Horwinski et al. |
| 4,407,303 A | 10/1983 | Akerstrom |
| 4,569,351 A | 2/1986 | Tang |
| 4,585,005 A | 4/1986 | Lue et al. |
| 4,585,013 A | 4/1986 | Harris |
| 4,607,639 A | 8/1986 | Tanagho et al. |
| 4,703,755 A | 11/1987 | Tanagho et al. |

(Continued)

OTHER PUBLICATIONS

2005 Biocontrol Medical article: "Lower Urinary Tract," Israel Nissenkom and Peter R. De Jong, pp. 1253-1258.

(Continued)

*Primary Examiner*—Kennedy J. Schaetzle
(74) *Attorney, Agent, or Firm*—Ryan Krumholz & Manion, S.C.

(57) ABSTRACT

Systems and methods provide a stimulation electrode assembly comprising an elongated lead sized and configured to be implanted within an adipose tissue region. The lead includes an electrically conductive portion to apply electrical stimulation to nerve or muscle in the adipose tissue region and at least one expandable anchoring structure deployable from the lead to engage adipose tissue and resist dislodgment and/or migration of the electrically conductive portion within the adipose tissue region.

20 Claims, 22 Drawing Sheets

U.S. PATENT DOCUMENTS

| | | |
|---|---|---|
| 4,716,888 A | 1/1988 | Wesner |
| 4,739,764 A | 4/1988 | Lue et al. |
| 4,771,779 A | 9/1988 | Tanagho et al. |
| 4,989,617 A | 2/1991 | Memberg et al. |
| 5,113,869 A | 5/1992 | Nappholz et al. |
| 5,154,172 A | 10/1992 | Terry, Jr. et al. |
| 5,215,086 A | 6/1993 | Terry, Jr. et al. |
| 5,222,494 A | 6/1993 | Baker, Jr. |
| 5,257,634 A | 11/1993 | Kroll |
| 5,282,845 A | 2/1994 | Bush et al. |
| 5,300,107 A | 4/1994 | Stokes et al. |
| 5,330,515 A | 7/1994 | Rutecki et al. |
| 5,344,439 A * | 9/1994 | Otten ............... 607/126 |
| 5,370,671 A | 12/1994 | Maurer et al. |
| 5,411,537 A | 5/1995 | Munshi et al. |
| 5,454,840 A | 10/1995 | Krakovsky et al. |
| 5,476,500 A | 12/1995 | Fain et al. |
| 5,562,717 A | 10/1996 | Tippey et al. |
| 5,588,960 A * | 12/1996 | Edwards et al. ............ 604/20 |
| 5,683,447 A | 11/1997 | Bush et al. |
| 5,722,999 A | 3/1998 | Snell |
| 5,733,322 A | 3/1998 | Starkebaum |
| 5,755,767 A | 5/1998 | Doan et al. |
| 5,922,015 A | 7/1999 | Schaldach |
| 5,984,854 A | 11/1999 | Ishikawa et al. |
| 6,055,456 A | 4/2000 | Gerber |
| 6,055,457 A | 4/2000 | Bonner |
| 6,061,596 A | 5/2000 | Richmond et al. |
| 6,091,995 A * | 7/2000 | Ingle et al. ............... 607/138 |
| 6,181,965 B1 | 1/2001 | Loeb et al. |
| 6,185,452 B1 | 2/2001 | Schulman et al. |
| 6,208,894 B1 | 3/2001 | Schulman et al. |
| 6,240,316 B1 | 5/2001 | Richmond et al. |
| 6,266,557 B1 | 7/2001 | Roe et al. |
| 6,308,101 B1 | 10/2001 | Faltys et al. |
| 6,345,202 B2 | 2/2002 | Richmond et al. |
| 6,360,750 B1 | 3/2002 | Gerber et al. |
| 6,381,496 B1 | 4/2002 | Meadows et al. |
| 6,432,037 B1 | 8/2002 | Eini et al. |
| 6,505,074 B2 * | 1/2003 | Boveja et al. ............. 607/41 |
| 6,510,347 B2 | 1/2003 | Borkan |
| 6,516,227 B1 | 2/2003 | Meadows et al. |
| 6,650,943 B1 | 11/2003 | Whitehurst et al. |
| 6,652,449 B1 | 11/2003 | Gross et al. |
| 6,684,109 B1 | 1/2004 | Osypka |
| 6,735,474 B1 | 5/2004 | Loeb et al. |
| 6,735,475 B1 | 5/2004 | Whitehurst et al. |
| 6,836,684 B1 | 12/2004 | Rijkhoff et al. |
| 6,862,480 B2 | 3/2005 | Cohen et al. |
| 6,907,293 B2 | 6/2005 | Grill et al. |
| 6,920,359 B2 | 7/2005 | Meadows et al. |
| 6,937,894 B1 | 8/2005 | Isaac et al. |
| 6,941,171 B2 | 9/2005 | Mann et al. |
| 6,999,819 B2 * | 2/2006 | Swoyer et al. ............ 607/117 |
| 7,047,078 B2 | 5/2006 | Boggs, II et al. |
| 2002/0055761 A1 | 5/2002 | Mann et al. |
| 2002/0055779 A1 | 5/2002 | Andrews |
| 2003/0004553 A1 | 1/2003 | Grill et al. |
| 2003/0018365 A1 | 1/2003 | Loeb |
| 2003/0100930 A1 | 5/2003 | Cohen et al. |
| 2003/0114905 A1 | 6/2003 | Kuzma |
| 2004/0030360 A1 | 2/2004 | Eini et al. |
| 2004/0088024 A1 | 5/2004 | Firlik et al. |
| 2004/0093093 A1 | 5/2004 | Andrews |
| 2004/0111126 A1 | 6/2004 | Tanagho et al. |
| 2004/0162594 A1 | 8/2004 | King |
| 2005/0055063 A1 | 3/2005 | Loeb et al. |
| 2005/0143787 A1 | 6/2005 | Boveja et al. |
| 2005/0149146 A1 | 7/2005 | Boveja et al. |
| 2006/0025829 A1 | 2/2006 | Armstrong et al. |

OTHER PUBLICATIONS

Mar. 2002 Physician's Manual; Cyberonics Model 201 NeuroCybernetic Prosthesis (NCP) Programming Wand, pp. 1-18.

Aug. 2002 Physician's Manual; Cyberonics Models 100 and 101 NeuroCybernetic Prosthesis System, NCP Pulse Generator, pp. 1-92.

2005 Advanced Neuromodulation Systems, Inc.; ANS Medical—Determining chronic pain causes and treatments; website: http://www.ans-medical.com/medicalprofessional/physician/rechargeableipgsystems.cfm.

Sweeney, J.D., D.A. Ksienski, J.T. Mortimer (1990) A nerve cuff technique for selective excitation of peripheral nerve trunk regions. IEEE Trans. Biomed. Eng. 37:706-715.

2004 Advanced Bionics Corpporation Summary of Safety and Effectiveness, pp. 1-18.

2004 Advanced Bionics Corporation Physician Implant Manual.

2005 Cyberonics VNS Therapy website: http://www.vnstherapy.com/Epilepsy/hcp/forsurgeons/implantedcomponents.aspx.

2004 Advanced Bionics Corporation Patient System Handbook.

Oct. 2001 Advanced Neuromodulation Systems, Inc. ANS Genesis Neurostimulation System Programmer User's Guide.

Nov. 21, 2001 Advanced Neuromodulation Systems, Inc. (ANS) Summary of Safety and Effectiveness Data, pp. 1-17.

Starbuck, D.L., Mortimer, J.T., Sheally C.N., Reswick, J.B. (1966) An implantable electrodes system for nerve stimulation, Proc. 19th Ann. Conf. on Eng. in Med. and Biol. 8:38.

Grill, W.M., J.T. Mortimer (1996) Quantification of recruitment properties of multiple contact cuff electrodes. IEEE Transactions on Rehabilitation Engineering 4(2):49-62.

Veraart, C., W.M. Grill, J.T. Mortimer (1993) Selective control of muscle activation with a multipolar nerve cuff electrode, IEEE Trans. Biomed. Engineering 40:640-653.

Grill, W.M. (2001) "Selective Activation of the Nervous System for Motor System Neural Prostheses" in Intel-ligent Systems and Technologies in Rehabilitation Engineering, H.-N.L. Teodorescu, L.C. Jain, Eds., CRC Press, 211-241.

McNeal, D.R., B.R. Bowman (1985) Selective activation of muscles using peripheral nerve electrodes. Med. and Biol. Eng. and Comp. 23:249-253.

Starbuck, D.L. (1965) Myo-electric control of paralyzed muscles. IEEE Transactions on Biomedical Engineering 12(3):169-172, Jul.-Oct.

Caldwell, C. (1971) Multielectrode Electrical Stimulation of Nerve, in Development of Orthotic Systems using Functional Electrical Stimulation and Myoelectric Control, Final Report Project #19-P-58391-F-01, University of Lubljana, Faculty of Electrical Engineering, Lubljana, Yugoslavia.

McNeal, D.R. (1974) Selective stimulation, in Annual reports of Progress, Rehabilitaiton Engineering Center, Ranchio Los Amigos Hospital, Downey, CA, pp. 24-25.

Wheeler et al.; "Management of incontienent SCI patients with penile stimulation; preliminary results," J Am Paraplegia Soc. Apr. 1994; 17(2):55-9.

U.S. Appl. No. 60/486,573, filed Jul. 2003, Loeb et al.

"Neuromodulation of the lower urinary tract," Experimental Physiology, 84, 149-160. Craggs, M. & McFarlane, J. P. (1999).

"Detection and inhibition of hyper-reflexia-like bladder contractions in the cat by sacral nerve root recording and electrical stimulation," Neuroruloty and Urodynamics, 20(2), 215-230 Jezernik S., Grill, W. M. & Sinkjaer, T. (2001.

"Prolonged enhancement of the micturition reflex in the cat by repetitive stimulation of bladder afferents," Journal of Physiology, 517.2, 599-605; Jiang, C-H. & Lindstrom, S. (1999).

"Self-controlled dorsal penile nerve stimulation to inhibit bladder hyperreflexia in incomplete spinal injury: A case report," Arch Phys Med Rehabil, 83, 273-7; Lee, Y. H. & Creasey, G. H. (2002).

"Detrusor inhibition induced from mechanical stimulation of the anal region and from electrical stimulation of pudendal nerve afferents," Investigative Urology, 5, 374-8; Sundin, T., Carlsson, C-A. & Kock, N. G. (1974).

"Bladder inhibition by penile nerve stimulation in spinal cord injury patients," The Journal of Urology, 147(1), 100-3; Wheeler et al. (1992).

"Aberrant reflexes and function of the pelvic organs following spinal cord injury in man," M.D. Craggs et al.; Autonomic Neuroscience: Basic & Clinical; 126-127 (2006) 355-370.

"Emerging clinical applications of electrical stimulation: opportunities for restoration of function," Grill et al.; Journal of Rehabilitation Research and Development, vol. 38 No. 6, Nov./Dec. 2001.

Bemelmans, Bart L H et al., "Neuromodulation by Implant for Treating Lower Urinary Tract Symptoms and Dysfunction", Eur Urol, 1999 Aug. 36(2): 81-91.

Bower WF et al., "A Urodynamic Study of Surface Neuromodulation versus Sham in Detrusor Instability and Sensory Urgency", J. Urology 1998; 160: 2133-2136.

Brindley, G. et al., "Sacral Anterior Root Stimulators for Bladder Control in Paraplegia", Paraplegia 1982; 20(6):365-381.

Dalmose AL et al., "Conditional Stimulation of the Dorsal Penile/Clitoral Nerve", Neurourol Urodyn 2003; 33(2): 130-37.

Fossberg E et al., "Maximal Electrical Stimulation in the Treatment of Unstable Detrusor and Urge Incontinence", Eur Urol 1990; 18: 120-123.

Gustafson K et al., "A Catheter Based Method to Activate Urethral Sensory Nerve Fibers", J Urol 2003; 170(1):126-129.

Gustafson K et al., "A Urethral Afferent Mediated Excitatory Bladder Reflex Exists in Humans", Neurosci Lett 2004; 360(1-2):9-12.

Jezernik S et al., "Electrical Stimulation for the Treatment of Bladder Dysfunction; Current Status and Future Possibilities", Neurol Res 2002; 24:413-30.

Jiang C et al., "Prolonged Increase in Micturition Threshold Volume by Anogenital Afferent Stimulation in the Rat", Br J Urol 1998; 82(3):398-403.

Juenemann K et al., "Clinical Significance of Sacral and Pudendal Nerve Anatomy", J Urol 1988; 139(1):74-80.

Madersbacher, H, "Urinary Urge and Reflex Incontinence", Urologe A 1991; 30(4): 215-222 (Abstract only - Article in German).

Mazieres, L et al., "The C Fibre Reflex of the Cat Urinary Bladder", J Physiol 1998; 513 (Pt 2):531-541.

Mazieres, L et al., "Bladder Parasympathetic Response to Electrical Stimulation of Urethral Afferents in the Cat", Neurol Urodynam 1997; 16: 471-472.

Nakamura et al., "Bladder Inhibition by Penile Electrical Stimulation", Br J Urol 1984; 56: 413-415.

Oliver, S et al., "Measuring the Sensations of Urge and Bladder Filing During Cystometry in Urge Incontinence and the Effects of Neuromodulation", Neurourol Urodyn 2003; 22: 7-16.

Previnaire JG et al., "Short-Term Effect of Pudendal Nerve Electrical Stimulation on Detrusor Hyperreflexia in Spinal Cord Injury Patients: Importance of Current Strength", Paraplegia 1996; 34: 95-99.

Rijkhoff N et al., "Urinary Bladder Control by Electrical Stimulation: Reiew of Electrical Stimulation Techniques in Spinal Cord Injury", Neurourol Urodyn 1997; 16(1):39-53.

Schmidt, Ra, "Applications of Neurostimulation in Urology", 1988; 7:585-92.

Spinelli, M et al., "A New Minimally Invasive Procedure for Pudendal Nerve Stimulation to Treat Neurogenic Bladder: Description of the Method and Preliminary Data", Neurourol and Urodyn. 2005; 24:305-309.

Talaat, M., "Afferent Impulses in the Nerves Supplying the Urinary Bladder", Journal of Physiology 1937; 89:1-13.

Tanagho, Ea et al., "Electrical Stimulation in the Clinical Management of the Neurogenic Bladder", J Urol. 1988; 140:1331-1339.

Vodusek, DB et al., "Detrusor Inhibition Induced by Stimulation of Pudendal Nerve Afferents", Neuroul and Urodyn. 1986; 5:381-389.

Yang, C. et al., "Peripheral Distribution of the Human Dorsal Nerve of the Penis", J Urol. 1998; 159(6):1912-6; discussion 1916.

* cited by examiner

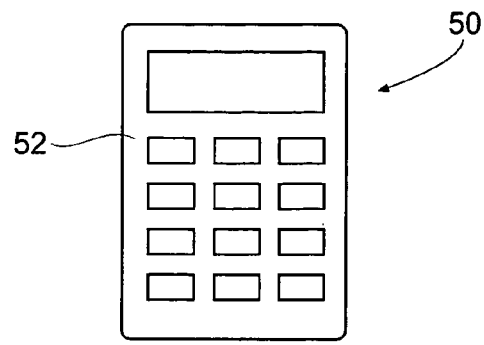
Fig. 4
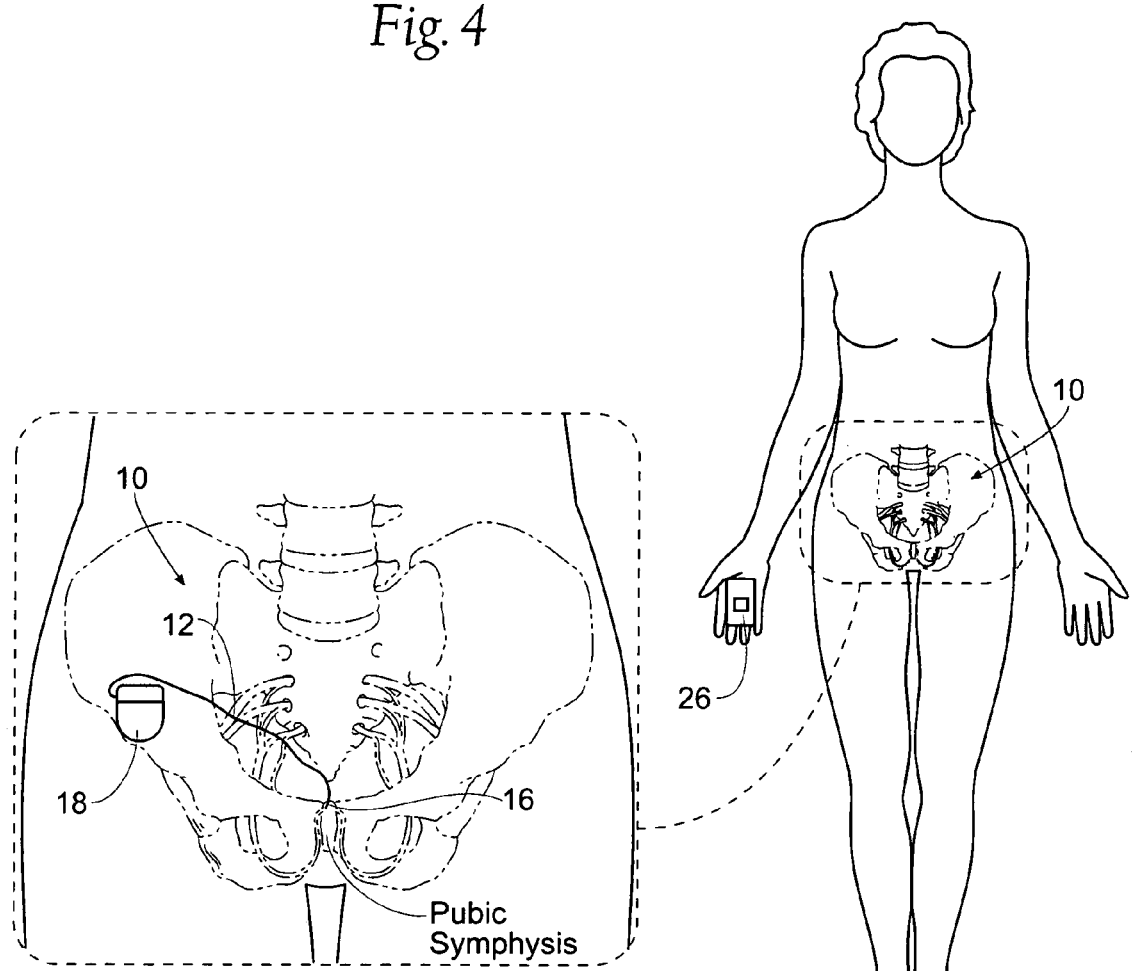
Fig. 5B
Fig. 5A

METHOD FOR AFFECTING URINARY FUNCTION WITH ELECTRODE IMPLANTATION IN ADIPOSE TISSUE

RELATED APPLICATIONS

This application claims the benefit of U.S. Provisional Patent Application Ser. No. 60/578,742, filed Jun. 10, 2004, and entitled "Systems and Methods for Bilateral Stimulation of Left and Right Branches of the Dorsal Genital Nerves to Treat Dysfunctions, Such as Urinary Incontinence." This application is also a continuation-in-part of co-pending U.S. patent application Ser. No. 10/777,771, filed Feb. 12, 2004, now U.S. Pat. No. 7,120,499, dated Oct. 10, 2006, and entitled "Portable Percutaneous Assemblies, Systems, and Methods for Providing Highly Selective Functional or Therapeutic Neurostimulation."

STATEMENT REGARDING FEDERALLY SPONSORED RESEARCH

This invention was made with government support under grant numbers 1R43AG021851-01 awarded by the National Institutes of Health, through the National Institute of Aging, and 1R43AG022292-01 awarded by the National Institutes of Health, through the National Institute of Aging. The Government has certain rights in the invention.

FIELD OF THE INVENTION

This invention relates to systems and methods for stimulating nerves and muscles in animals, including humans.

BACKGROUND OF THE INVENTION

Thirteen million Americans suffer from various types of urinary incontinence.

The most prevalent type of urinary incontinence (22% of the total) is called Stress Incontinence (SUI). SUI is characterized by the unintended emission of urine during everyday activities and events, such as laughing, coughing, sneezing, exercising, or lifting. These activities and events cause an increase in bladder pressure resulting in loss of urine due to inadequate contraction of the sphincter muscle around the outlet of the bladder.

Another prevalent type of urinary incontinence (18% of the total) is called Urinary Urge Incontinence (UUI). UUI is characterized by a strong desire to urinate, followed by involuntary contractions of the bladder. Because the bladder actually contracts, urine is released quickly, making it impossible for urge incontinence sufferers to predict when the problem will occur. UUI can be caused by infections, sphincter disorders, or nervous system disorders that affect the bladder.

Many people (47% of the total) encounter a combination of bladder control disorders.

Damage to the bladder, urethra, periurethral muscles and sphincters, nerves, and accessory organs can be experienced by women during childbirth or hysterectomy. This damage can lead to urinary incontinence. Prostate problems can lead to urinary incontinence in men. The number of people suffering from urinary incontinence is on the rise as the population ages.

Various treatment modalities for urinary incontinence have been developed. These modalities typically involve drugs, surgery, or both. Disposable pads can also used, not to treat the disorder, but to deal with its consequences.

Pharmocotherapy (with and without attendant behavioral therapy) appears to moderate the incidence of urinary incontinence episodes, but not eliminate them. Drug therapy alone can lead to a reduction of incontinence episodes after eight weeks by about 73%. When combined with behavioral therapy, the reduction after eight weeks is about 84% (Burgio et al, JAGS. 2000; 48:370-374). However, others have questioned the clinical significance of the results, noting that the differences in outcomes using anticholinergic drugs and placebo were small, apart from the increased rate of dry mouth in patients receiving active treatment (Herbison P, Hay-Smith J, Ellis J, Moore K, BMJ 2003; 326:841).

One present surgical modality involves the posterior installation by a percutaneous needle of electrodes through the muscles and ligaments over the S3 spinal foramen near the right or left sacral nerve roots (InterStim™ Treatment, Medtronic). The electrodes are connected to a remote neurostimulator implantable pulse generator implanted in a subcutaneous pocket on the right hip to provide unilateral spinal nerve stimulation. This surgical procedure near the spine is complex and requires the skills of specialized medical personnel. Furthermore, in terms of outcomes, the modality has demonstrated limited effectiveness. For people suffering from UUI, less than 50% have remained dry following the surgical procedure. In terms of frequency of incontinence episodes, less than 67% of people undergoing the surgical procedure reduced the number of voids by greater than 50%, and less than 69% reduced the number of voids to normal levels (4 to 7 per day). This modality has also demonstrated limited reliability. Fifty-two percent (52%) of people undergoing this surgical procedure have experienced therapy-related adverse events, and of these 54% required hospitalization or surgery to resolve the issue. Many (33%) require surgical revisions.

It has been reported that 64% of people undergoing some form of treatment for urinary incontinence are not satisfied with their current treatment modality (National Association for Incontinence, 1988).

A recently proposed alternative surgical modality (Advanced Bionics Corporation) entails the implantation through a 12 gauge hypodermic needle of an integrated neurostimulator and bi-polar electrode 16 assembly (called the Bion® System) through the perineum into tissue near the pudendal nerve on the left side adjacent the ischial spine. See, e.g., Mann et al, Published Patent Application US2002/0055761. The clinical effectiveness of this modality is not known.

There remains a need for systems and methods that can restore urinary continence, in a straightforward manner, without requiring drug therapy and complicated surgical procedures.

SUMMARY OF THE INVENTION

One aspect of the invention provides systems and methods that include a stimulation electrode assembly comprising an elongated lead sized and configured to be implanted within an adipose tissue region. The lead includes an electrically conductive portion to apply electrical stimulation to nerve or muscle in the adipose tissue region and at least one expandable anchoring structure deployable from the lead to engage adipose tissue and resist dislodgment and/or migration of the electrically conductive portion within the adipose tissue region.

Another aspect of the invention provides a functional kit for the stimulation electrode assembly, together with instructions for implanting and operating the assembly in a targeted adipose tissue region.

Other features and advantages of the inventions are set forth in the following specification and attached drawings.

BRIEF DESCRIPTION OF THE DRAWINGS

FIG. 4 is a plane view of a clinical programmer that can be used in conjunction with the system shown in FIG. 1.

FIGS. 5A and 5B are anterior anatomic views of the system shown in FIG. 1 after implantation in an adipose tissue region at or near the pubic symphysis.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with the treatment of urinary incontinence by the bilateral stimulation of the left and/or right branches of the dorsal genital nerves using a single lead implanted in adipose or other tissue in the region at or near the pubic symphysis. That is because the features and advantages of the invention are well suited for this purpose. Still, it should be appreciated that the various aspects of the invention can be applied in other forms and in other locations in the body to achieve other objectives as well.

I. System Overview

A. The Implant System

Figure 1:
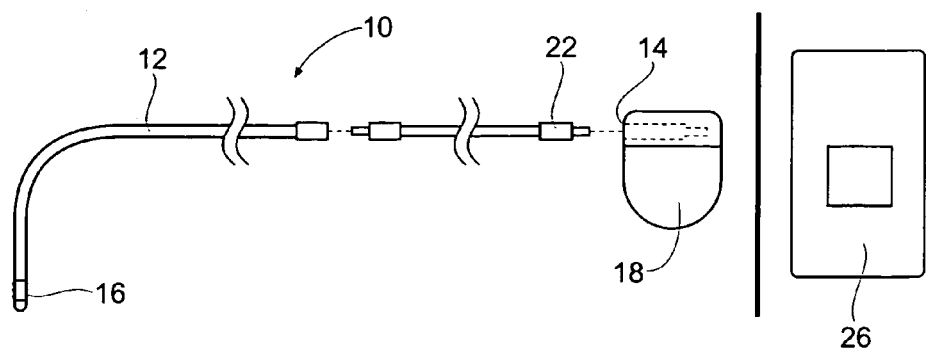
FIG. 1 is a plane view of an implant system for treating urinary incontinence in humans.

FIG. 1 shows an implant system 10 for treating urinary incontinence in humans.

The implant system 10 includes an implantable lead 12 having a proximal and a distal end. The proximal end carries a plug 22, which is desirably of an industry-standard size, for coupling to an industry-sized connector 14 on a implantable pulse generator 18. The distal end includes at least one electrically conductive surface, which will also in shorthand be called an electrode 16. The lead electrically connects the electrode 16 to the connector 14, and this to the implantable pulse generator 18 itself, while electrically insulating the wire from the body tissue except at the electrode 16.

The lead 12 and electrode 16 are sized and configured to be implanted percutaneously in tissue, and to be tolerated by an individual during extended use without pain or discomfort. The comfort is both in terms of the individual's sensory perception of the electrical waveforms that the electrode applies, as well as the individual's sensory perception of the physical presence of the electrode and lead. In both categories, the lead 12 and electrode 16 are desirably "imperceptible."

In particular, the lead 12 and electrode 16 are sized and configured to reside with stability in soft or adipose tissue 54 in the lower anterior pelvic region of the body (see FIG. 5). It has been discovered that, when properly placed in this region, a single lead/electrode 16 is uniquely able to deliver electrical stimulation current simultaneously to both left and right branches of the dorsal genital nerves, present near the clitoris in a female and near the base of the penis of a male (see FIGS. 5A and 5B). Specific features of the lead 12 and electrode 16 that make them well suited for this purpose, as well as other purposes, will be described in greater detail later.

The implant system 10 also includes an implantable pulse generator 18. The implantable pulse generator 18 includes a circuit that generates electrical stimulation waveforms. An on-board battery provides the power. The implantable pulse generator 18 also includes an on-board, programmable microprocessor, which carries embedded code. The code expresses pre-programmed rules or algorithms under which the desired electrical stimulation waveforms are generated by the circuit. The metal case of the implantable pulse generator also serves as the return electrode for the stimulus current introduced by the lead/electrode when operated in a monopolar configuration.

The implantable pulse generator 18 is sized and configured to be implanted subcutaneously in tissue, desirably in a subcutaneous pocket remote from the electrode 16 and using a minimally invasive surgical procedure. As shown in FIGS. 5A and 5B, the implantation site can comprise a tissue region on the posterior hip. Alternatively, the implantation site can comprise a more medial tissue region in the lower abdomen. There, the implantable pulse generator 18 can reside for extended use without causing pain and/or discomfort and/or without effecting body image.

Figure 32:
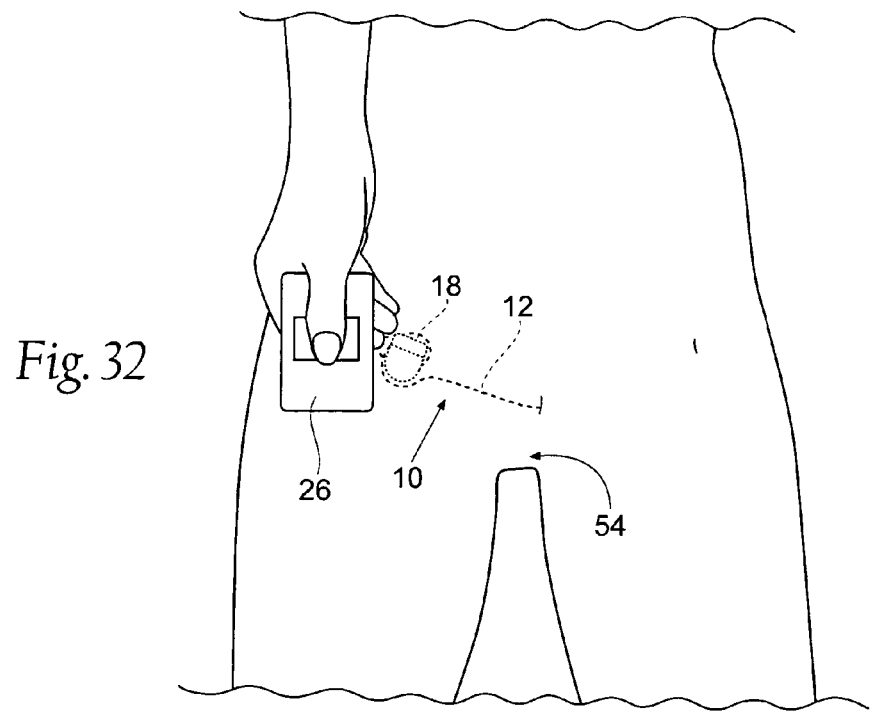
FIG. 32 is an anterior anatomic view of the system shown in FIG. 1 after implantation, showing the use of a controller to operate the system.

The implant system 10 includes an external patient controller 26 (see FIG. 5A also). The controller 26 is sized and configured to be held by the individual to transcutaneously activate and deactivate or modify the output of the implantable pulse generator. The controller 26 may, e.g., be a simple magnet that, when placed near the site where the implantable pulse generator 18 is implanted (see FIG. 32), toggles a magnetic switch within the implantable pulse generator 18 between an on condition and an off condition, or advances through a sequence of alternative stimulus modes pre-programmed by the clinician into implantable pulse generator 18. Alternatively, the controller 26 may comprise more sophisticated circuitry that would allow the individual to make these selections through an RF field (magnetic and/or electric) that passes through the skin and tissue within an arm's length distance from the implantable pulse generator.

According to its programmed rules, when switched on, the implantable pulse generator 18 generates prescribed stimulation waveforms through the lead 12 and to the electrode 16. These waveforms bilaterally stimulate the left and right branches of the dorsal genital nerves in a manner that achieves the desired physiologic response.

It has been discovered that bilateral stimulation of the dorsal genital nerves achieved by placement of a single electrode 16 at a unique location in the body (which will be described m greater detail later), achieves the desired physiologic result of consistently and effectively inhibiting unwanted bladder contractions. This makes possible the treatment of UUI and/or mixed UUI and SUI or other urinary continence dysfunctions. Using the controller 26, the individual may turn on or turn off the continence control waveforms at will or adjust the strength, depending, e.g., upon the time of day or fluid consumption.

B. Physician Surgical Tools

The implant system 10 shown in FIG. 1 makes desirable a system of physician surgical tools (shown in FIG. 2) to facilitate implantation of the implant system 10 in the intended way, desirably on an outpatient basis.

Figure 2:
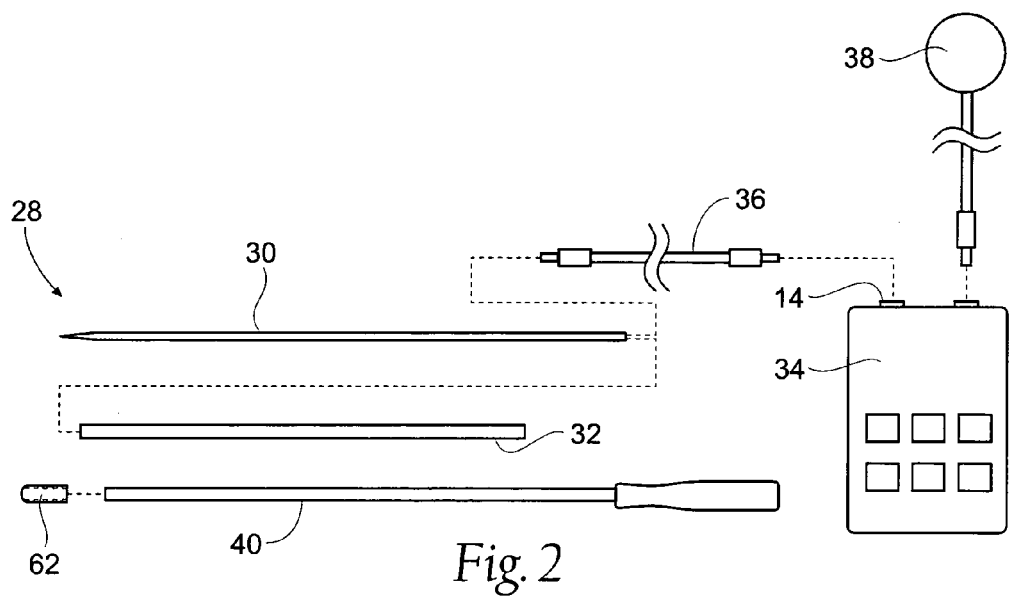
FIG. 2 is a plane view of a system of surgical tools that can be use to implant the system shown in FIG. 1.

The surgical tool system 28 shown in FIG. 2 includes a needle 30 (or trocar) and a companion introducer sleeve 32. The sleeve 32 is electrically insulated or insulated except at its tip. The needle 30 is also electrically insulated, except at its tip.

The tool system 28 also includes an external pulse generator 34, which operates to generate stimulation wave pulses of the same type as the implantable pulse generator 18. The external pulse generator 34 includes a connector cable 36 to couple the external pulse generator 34 to the needle 30. A patch electrode 38 is also included, which is to be placed on the skin of the individual and coupled to the external pulse generator 34, to serve as a return path for the stimulation waveforms. In use (as will be described in greater detail later), and with the individual subject to anesthesia, the needle 30 is placed tip-first into the sleeve 32, and the sleeve 32 and needle 30 are advanced percutaneously into the targeted tissue region in the lower abdomen. The needle 30 and return electrode 38 are coupled to the external pulse generator 34, to apply stimulation waveforms through the tip of the needle concurrent with positioning of the needle 30.

By monitoring anal pressure and/or contractions, patient-reported sensations, and/or bladder contractions in concert with applying stimulation waveforms through the tip of the needle 30—e.g., using standard clinical urodynamic monitoring instruments—the physician can probe the tissue region, penetrating and withdrawing the needle 30 as necessary in a minimally invasive way, until a subcutaneous location where optimal intended stimulation results are realized.

Once this location is found, the needle 30 can be withdrawn from the sleeve 32, followed by insertion of the lead 12, electrode-first, through the sleeve 32 into the location. Then the sleeve 32 is withdrawn which fixes the location of the electrode 16, as will be described in greater detail later. Desirably, the external pulse generator 34 is coupled to the lead 12 through the cable 36 to confirm that the electrode 16 resides in the desired location before tunneling the lead.

The tool system 28 also includes a tunneling tool 40. In use (as will also be described later), and with an individual still possibly subject to only local anesthesia, the tunneling tool 40 is manipulated by the physician to route the lead 12 subcutaneously to the pocket site where the implantable pulse generator 18 is to be implanted. The lead 12 is coupled to the implantable pulse generator 18. The lead 12 and implantable pulse generator 18 are placed into the subcutaneous pocket, which is sutured closed.

Using the surgical tool system 28, the implant system 10 can be implanted in the manner shown in FIGS. 5A and 5B.

C. Test Screening Tools

In the above description, the surgical tool system 28 is used to implant the implant system 10 in a single surgical procedure. Alternatively, and desirably, a two-stage surgical procedure can be used.

The first stage comprises a screening phase that performs test stimulation using a temporary external pulse generator to evaluate if an individual is a suitable candidate for extended placement of the implantable pulse generator. The first stage can be conducted, e.g., during a nominal two week period. If the patient is a suitable candidate, the second stage can be scheduled, which is the implantation of the implantable pulse generator 18 itself, as described above.

A test screening system 42 (shown in FIG. 3) can be provided to facilitate the two stage procedure. The test screening system 42 includes the lead 12 and electrode 16, which are the same as those included with the implant system 10 shown in FIG. 1. The test screening system 42 also includes a percutaneous extension cable 44, which is sized and configured to be tunneled subcutaneously from the pocket site to a remote site (e.g. 5-10 cm medially) where it exits the skin. The percutaneous extension cable has a proximal and distal end. The proximal end carries a receptacle 46 for connection to the industry-standard size plug on the end of the lead 12. The distal end of the percutaneous extension cable 44 carries a plug 48 that couples to an external test cable 88, which itself is coupled to an external pulse generator 34, which the test screening system 42 further includes.

The external pulse generator 34 can also be of the same type previously described in connection with the surgical tool system 28. In this arrangement, the patch return electrode 38 is included, or is otherwise available, to be coupled to the external pulse generator 34. An alternative form of an external pulse generator 34, usable with the test screening system 42, will be described later.

The test screening system 42 also includes the external test cable 88. One end of the external test cable 88 carries a plug 90 to connect to the external pulse generator 34. The other end of the external test cable 88 includes a connector to receive the plug 48 of the percutaneous extension cable 44. This end of the external test cable 88 can also be sized and configured to connect directly to the surface patch electrode 38.

In use (as will be described in greater detail later), the physician makes use of the needle 30 and sleeve 32 of a surgical tool system 28 to implant the electrode 16 and lead 12 in the desired location, in the manner previously described. These components of a surgical tool system 28 can be provided with the test screening system 42. The percutaneous extension cable 44 is coupled to the lead 12. Using the tunneling tool 40 of a surgical tool system 28, the physician subcutaneously tunnels the percutaneous extension cable 44 to a suitable exit site, which is desirably remote from the site where the pocket for the implanted pulse generator is to be created in the second phase. Further details of this will be described in greater detail later. A short length of the percutaneous extension cable 44 that carries the plug 48 extends outside the exit site, for coupling the electrode 16 to the external pulse generator 34 via the test cable 88. The return patch electrode 38 is also coupled to the external pulse generator 34.

The individual patient wears the external pulse generator 34 and return patch electrode 38 for the prescribed test period. The external pulse generator 34 supplies the prescribed stimulation regime. If an improvement in urinary continence is achieved, the second phase is warranted. In the second phase, the percutaneous extension cable 44 is removed and discarded, and the implantable pulse generator is connected to the lead 12 and installed in a pocket remote from the electrode 16 in the manner previously described.

D. Clinician Tools

A clinical tool system 50 is desirably provided to condition the implantable pulse generator 18 to perform in the intended manner.

Figure 31:
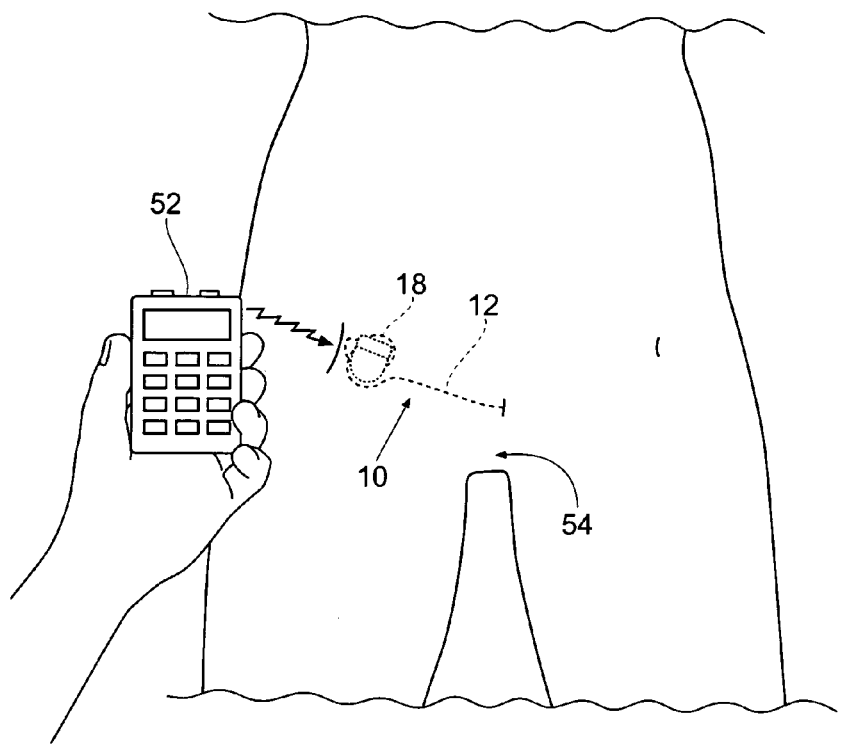
FIG. 31 is an anterior anatomic view of the system shown in FIG. 1 after implantation, showing the use of the clinical programmer shown in FIG. 4 to program the system.

In the embodiment shown in FIG. 4, the clinical tool system 50 includes a clinical programmer 52 and perhaps a separate wand connected to the programmer by a cable. The clinical programmer 52 can be placed into transcutaneous communication with an implantable pulse generator 18, e.g., through a radio-frequency magnetic and/or electric field (see FIG. 31), or using a wand. The clinical programmer 52 may incorporate a custom program operating on a handheld computer or other personal digital appliance (PDA). Should a personal digital appliance be used with a custom program, then the circuitry necessary to generate and detect the RF fields used to communicate with the implantable pulse generator would be located in the wand. The clinical programmer 52 or PDA includes an on-board microprocessor powered by a rechargeable, on-board battery (not shown). The microprocessor carries embedded code which may include pre-programmed rules or algorithms that allow a clinician to remotely download program stimulus parameters and stimulus sequences parameters into the implantable pulse generator. The microprocessor of the clinical programmer 52 is also desirably able to interrogate the implantable pulse generator and upload operational data from the implanrable pulse generator.

II. Implanting the Implant System

A. The Anatomic Landmarks

As already described, certain components of the implant system 10 are sized and configured to be implanted in adipose tissue in a particular location in an individual's lower abdomen, where it has been discovered that effective bilateral stimulation of both the left and right branches of the dorsal genital nerves can be achieved with a single electrode. The main anatomic landmark guiding the unique placement of these components is the pubic symphysis.

Figure 6:
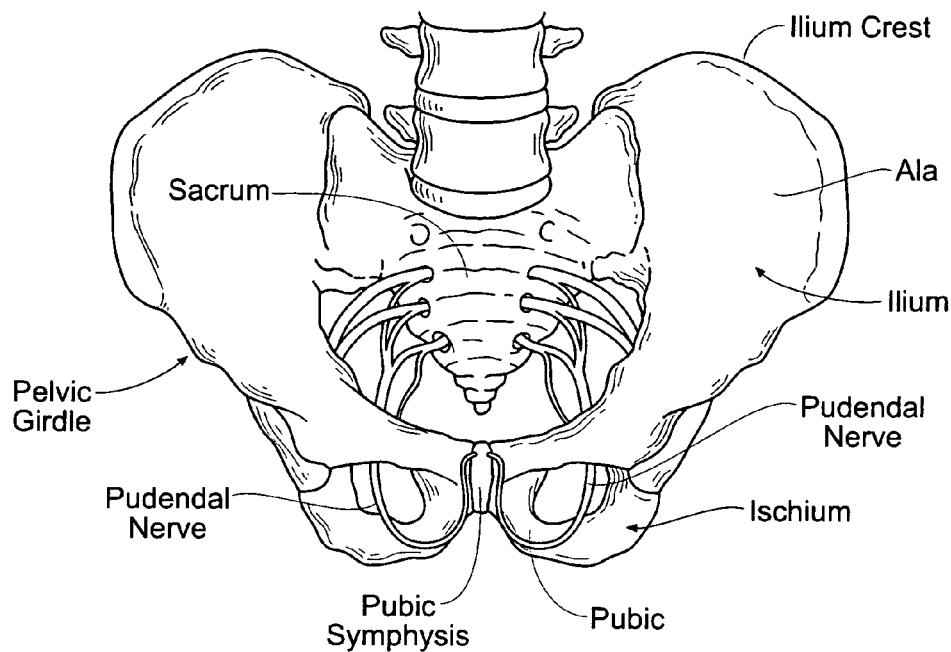
FIG. 6 is an anterior anatomic view of the pelvic girdle in a human.

As FIG. 6 shows, the hip bones are two large, irregularly shaped bones, each of which develops from the fusion of three bones, the ilium, ischium, and pubis. The ilium is the superior, fan-shaped part of the hip bone. The ala of the ilium represents the spread of the fan. The ilium crest represents the rim of the fan. It has a curve that follows the contour of the ala between the anterior and posterior superior iliac spines.

Figure 7:
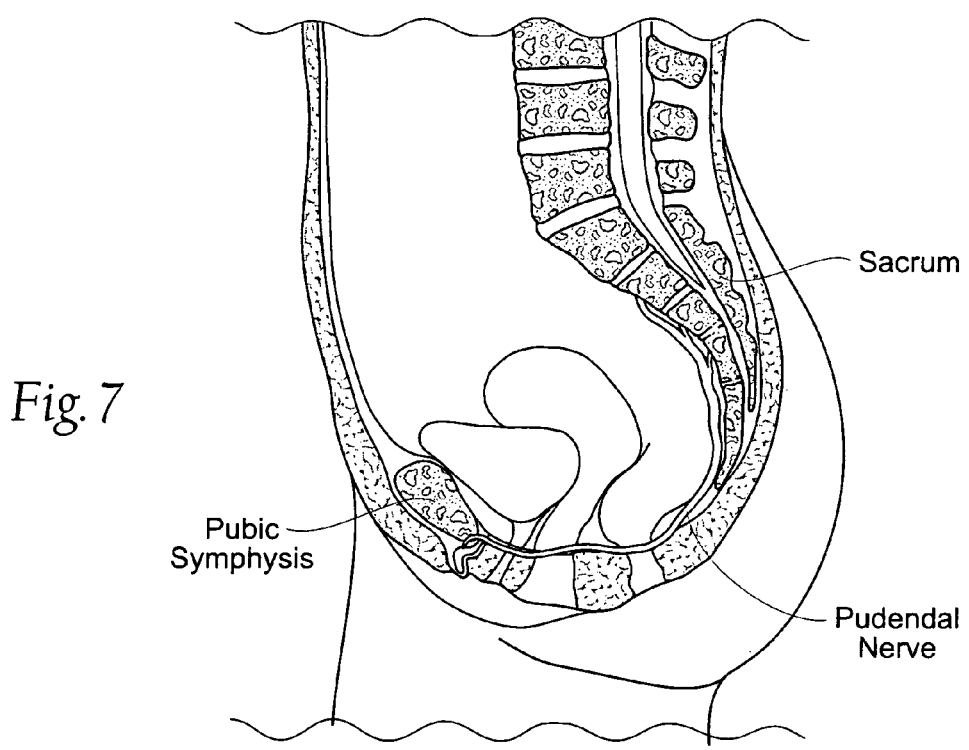
FIG. 7 is a lateral section view of the pelvic girdle region shown in FIG. 6.

As FIGS. 6 and 7 show, the sacrum is formed by the fusion of five originally separate sacral vertebrae. The hip bones are joined at the pubic symphysis anteriorly and to the sacrum posteriorly to form the pelvic girdle (see FIG. 6). The pelvic girdle is attached to the lower limbs. Located within the pelvic girdle are the abdominal viscera (e.g., the ileum and sigmoid colon) and the pelvic viscera (e.g., the urinary bladder and female reproductive organs such as the uterus and ovaries).

Within this bony frame (see FIGS. 6 and 7), the pudendal nerve is derived at the sacral plexus from the anterior divisions of the ventral rami of S2 through S4. The pudendal nerve extends bilaterally, in separate branches on left and right sides of the pelvic girdle. Each branch accompanies the interior pudendal artery and leaves the pelvis through the left and right greater sciatic foramens between the piriformis and coccygeus muscles. The branches hook around the ischial spine and sacrospinous ligament and enter the skin and muscles of the perineum through the left and right lesser sciatic foramen.

Figure 8:
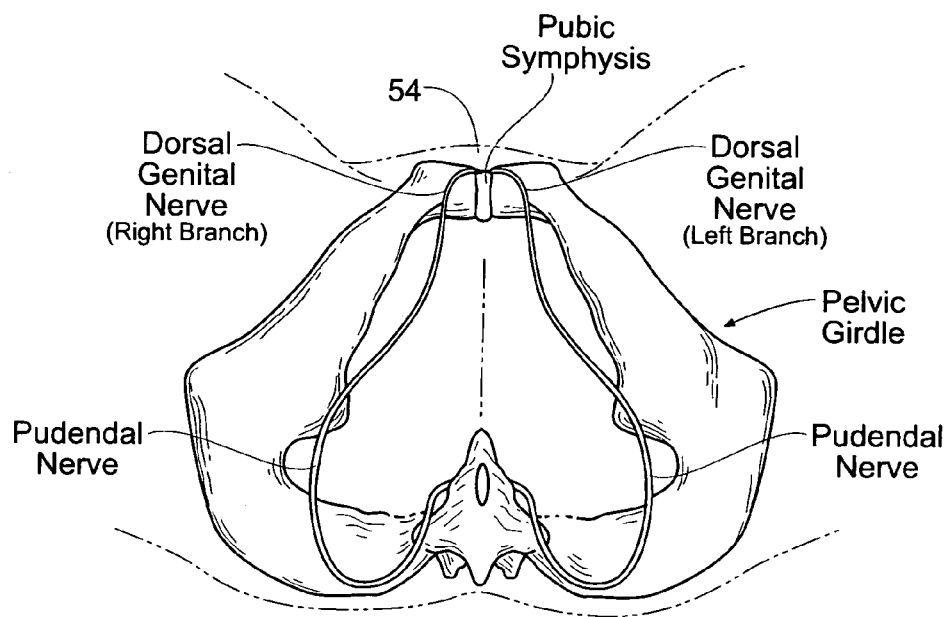
FIG. 8 is an inferior view of the pelvic girdle region shown in FIG. 6.

As shown in FIG. 8, the bilateral left and right braches extend anteriorly through the perineum, each ending as the dorsal genital nerve of the penis or clitoris. The genital nerves are the chief sensory nerve of the external genitalia. The FIGS. are largely based upon the anatomy of a female, but the parts of the male perineum are homologues of the female.

As FIG. 8 shows, in the male and female, adipose tissue 54 overlays the pubic symphysis. The bilateral branches of the genital nerves innervate this tissue region. In the female, this tissue region is known as the mons pubis. In the male, the penis and scrotum extend from this region. Further discussion regarding the fixation of the lead 12 and electrode 16 in adipose tissue 54 will be described later.

B. Implantation Methodology

Representative surgical techniques will now be described to place an electrode 16 and lead 12 in a desired location m adipose tissue 54 at or near the pubic symphysis. It is this desired placement that makes possible the bilateral stimulation of both left and right branches of the dorsal genital nerves with a single lead 12 to provide continence.

Before implantation, it is recommended that an oral broad spectrum antibiotic is given and continued for 5 days. The lower abdomen from the pubic symphysis to umbilicus and from the anterior iliac spines bilaterally are prepped with Betadine (or Hibiclens Solutions for cases of Betadine allergy).

As before generally described, implantation of the implant system 10 shown in FIG. 1 can entail a single surgical procedure or a two-step surgical procedure. Each will now be described.

1. Single Surgical Procedure

FIGS. 9 to 20 illustrate steps of implanting an implant system 10 in a single surgical procedure.

Locating the Lead/Electrode

The site for the needle puncture 60 is located midline or near-midline, near the inferior border of the pubic symphysis aiming toward the clitoris (or the base of the penis in males). Local anesthesia—e.g., 1% Lidocaine (2-5 ccs) or equivalent—is injected prior to making the anticipated needle 30 puncture site.

Figure 9:
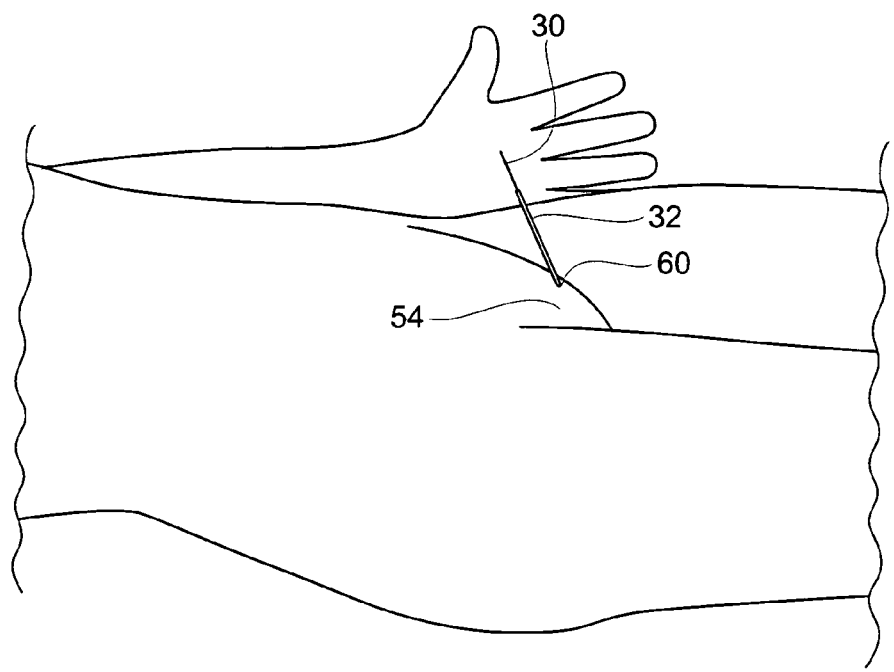
FIGS. 9 to 20 illustrate steps of implanting the system shown in FIG. 1 in a single surgical procedure.
Figure 10:
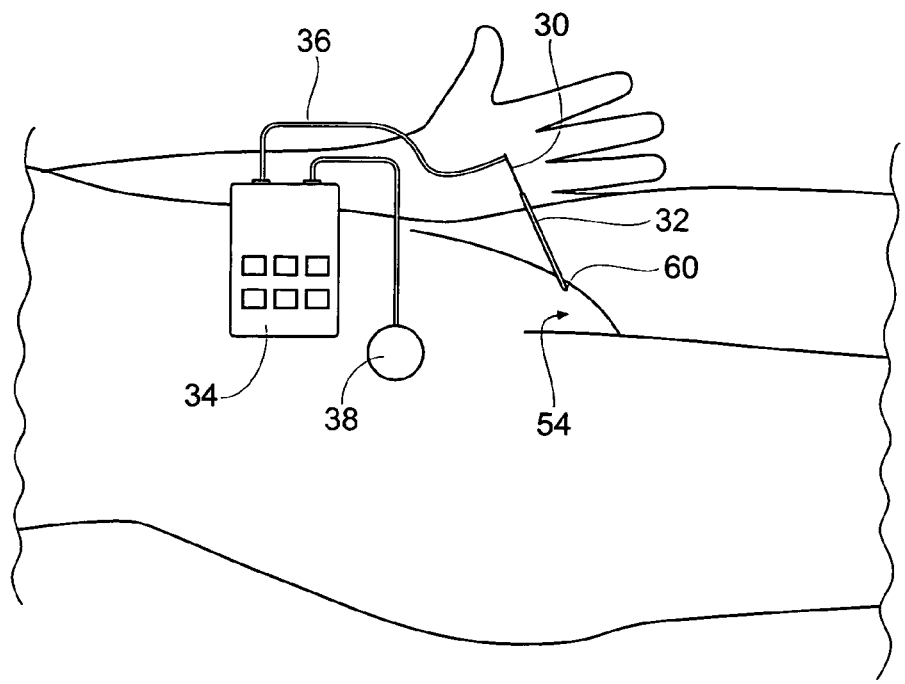

Once local anesthesia is established, as shown in FIG. 9, the needle 30 and sleeve 32 are advanced percutaneously into the anesthetized site 60 to a depth necessary to reach the target site between the pubic symphysis and the clitoris. As FIG. 10 shows, the needle 30 is coupled to the external pulse generator 34 (via the cable 36), to apply stimulation waveforms through the needle tip concurrent with positioning of the needle 30. A patch electrode 38 placed on the skin of the individual is also coupled to the external pulse generator 34 to serve as a return path for the stimulation waveforms.

The physician monitors anal pressure, and/or anal sphincter contractions, patient-reported sensations, and/or bladder contractions in concert with applying stimulation waveforms through the needle tip, penetrating and withdrawing the needle 30 as necessary m a nummally invasive way, until a subcutaneous location where bilateral stimulation of both left and right branches of the genital nerves results.

Figure 11:
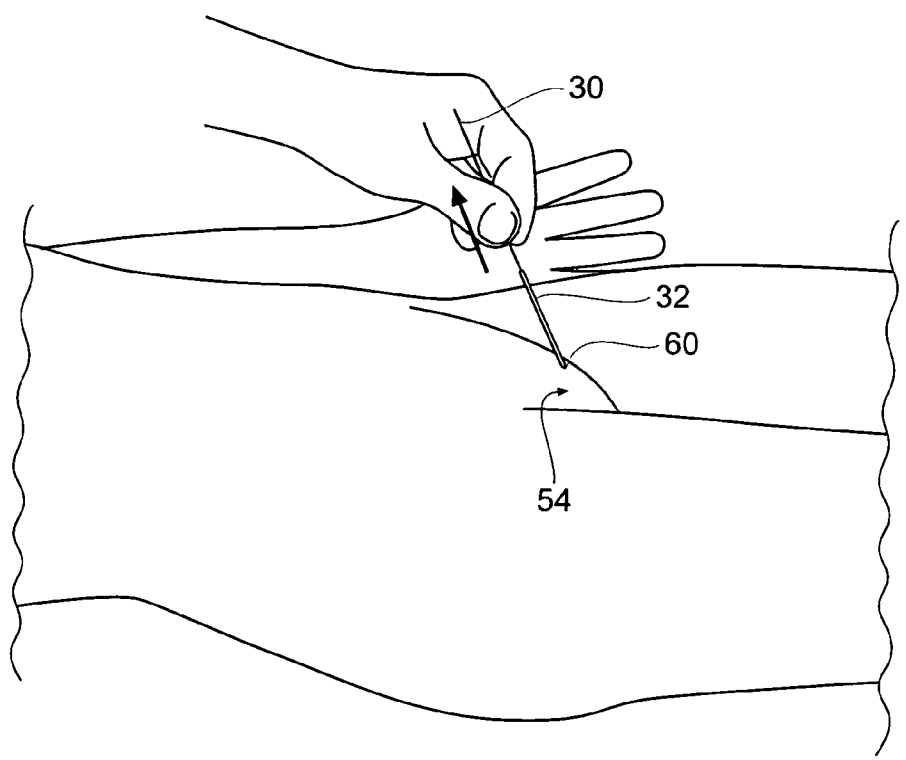
Figure 12:
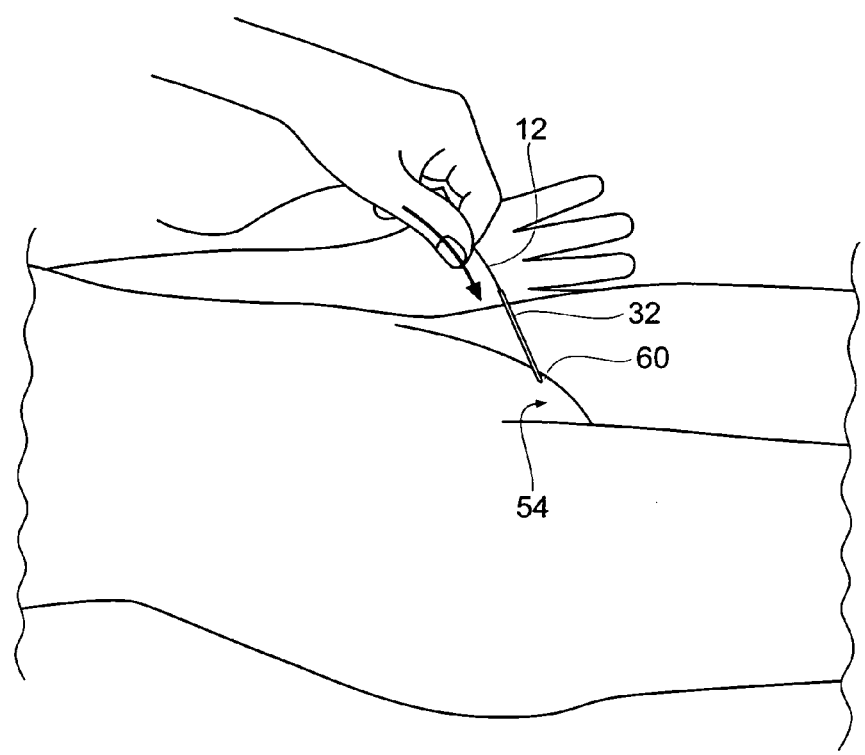
Figure 13:
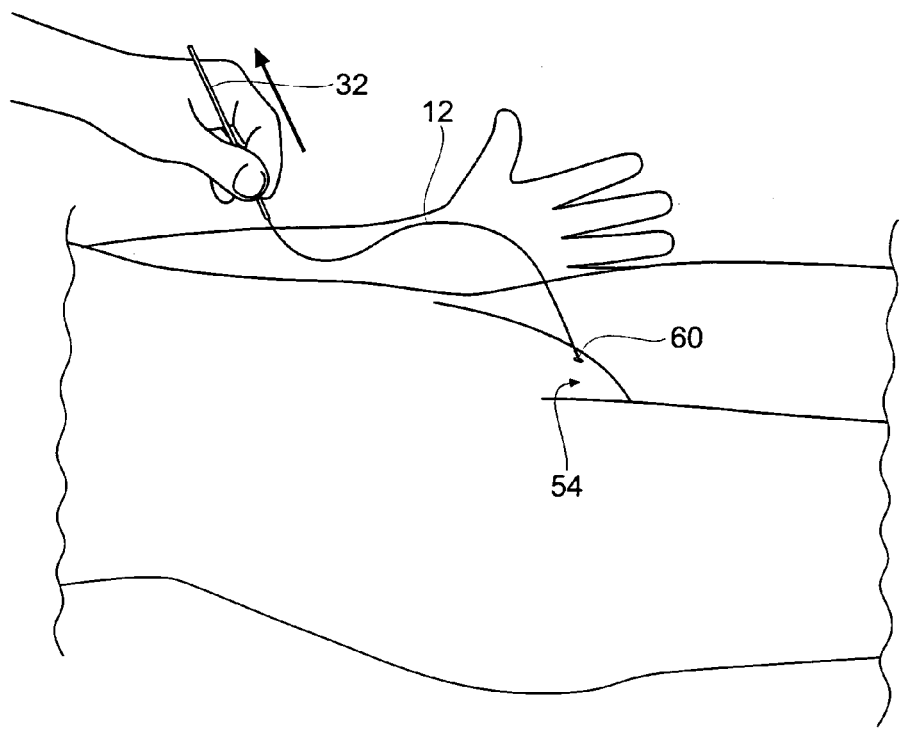
Figure 14:
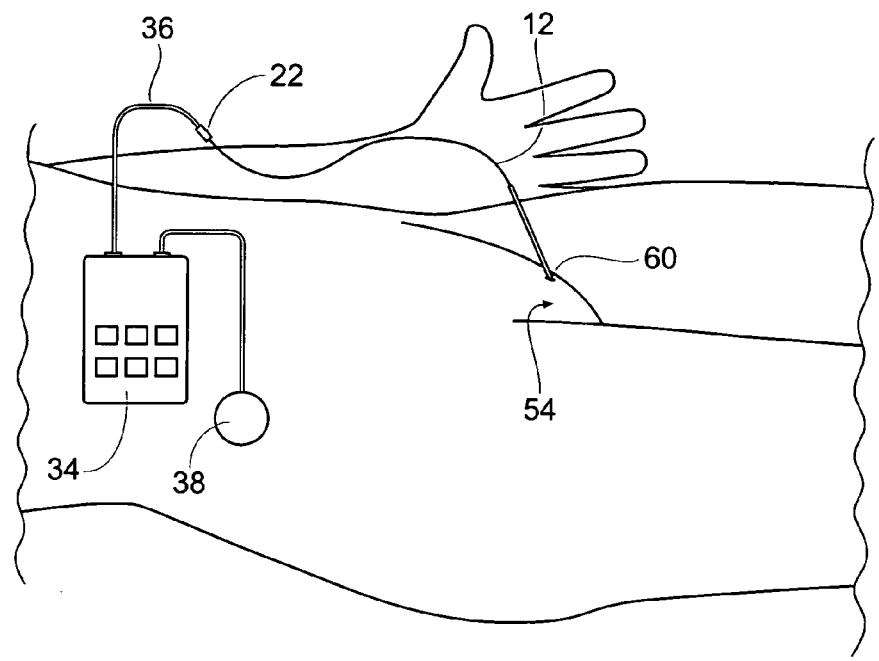

As FIG. 11 shows, once this location is found, the external pulse generator 34 is disconnected and the needle 30 is withdrawn from the sleeve 32. As FIG. 12 shows, the lead 12, electrode-first, is passed through the sleeve 32 into the location. As FIG. 13 shows, the introducing sleeve 32 is withdrawn, which fixes the location of the electrode 16. Desirably, the external pulse generator 34 is again coupled to the lead 12 via the cable 36 (see FIG. 14) to apply stimulation pulses through the electrode 16, to confirm that the electrode 16 resides in the location previously found. This aspect of the deployment of the electrode 16 will be described in greater detail later.

Forming the Implantable Pulse Generator Pocket

Figure 15:
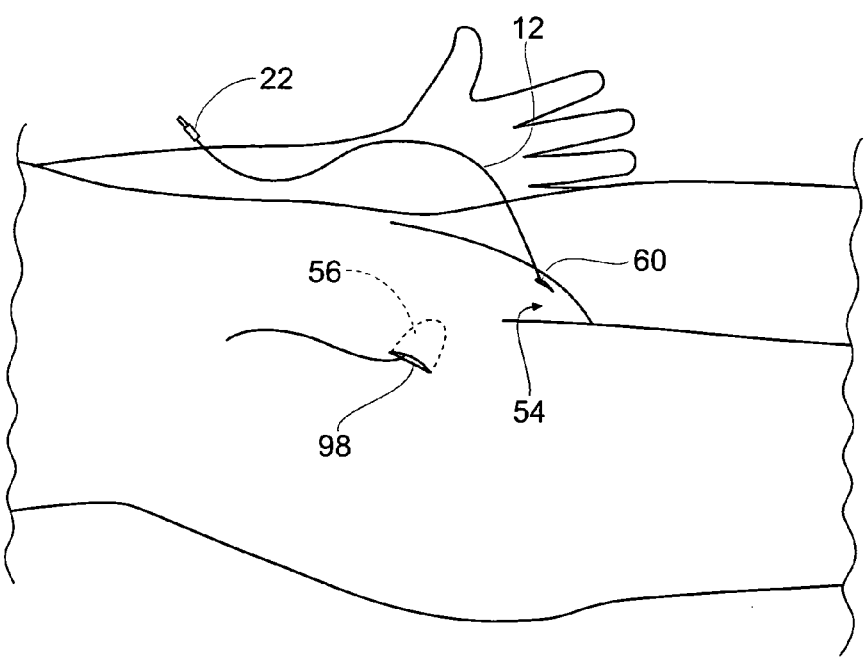
Figure 16:
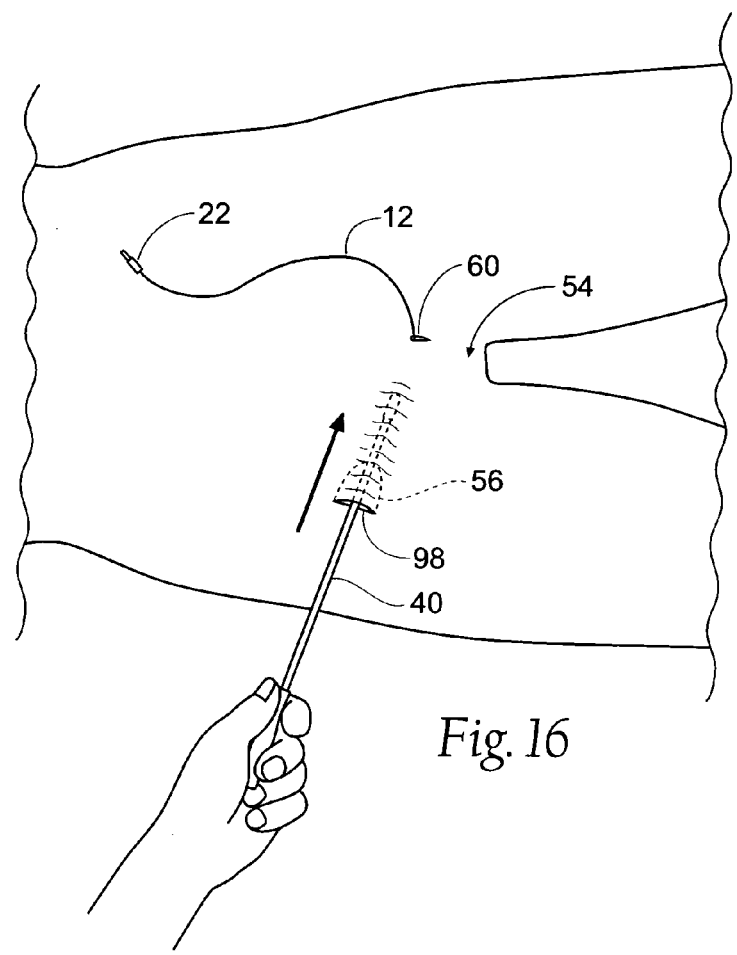

The incision site for forming the subcutaneous pocket 56 for the implantable pulse generator comprises a lateral 2 cm incision 98 (see FIG. 15), which, in FIG. 15, is located two finger-breaths medial to the anterior iliac spine and made in the direction of the dermatomal skin line. Local anesthesia—e.g., 1% Lidocaine (2-5 ccs) or equivalent—is injected before making the incision in this site.

Once local anesthesia is established, the incision for the pocket 56 is made using a skin knife. The incision is made large enough to accept the index or dissecting finger of the implant physician.

As FIG. 15 shows, a subcutaneous pocket 56 is made to accept the implantable pulse generator 18 using blunt dissection techniques of the subcutaneous tissues. The axis of the pocket 56 follows the direction of the dermatomal skin line and the entrance site of the lead 12/electrode 16.

Tunneling the Lead

Figure 17:
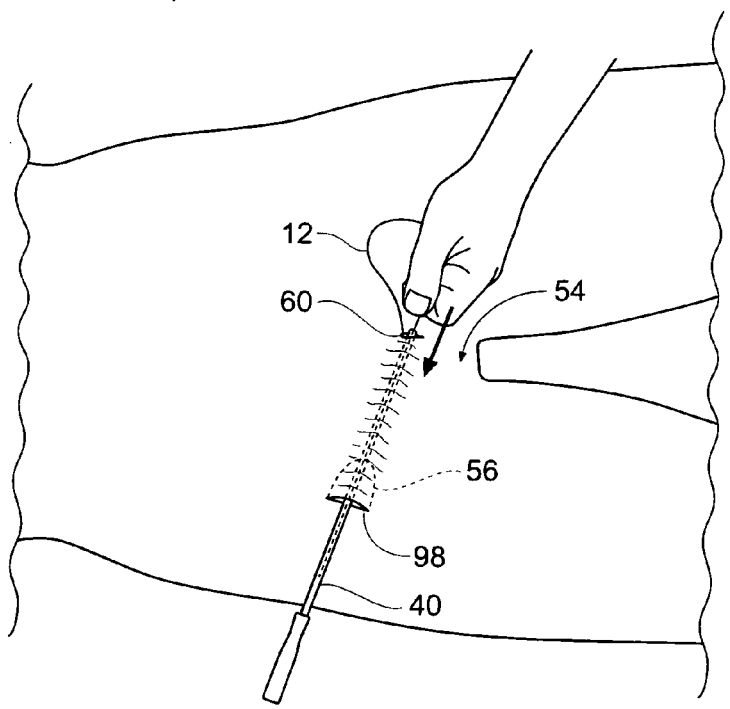
Figure 18:
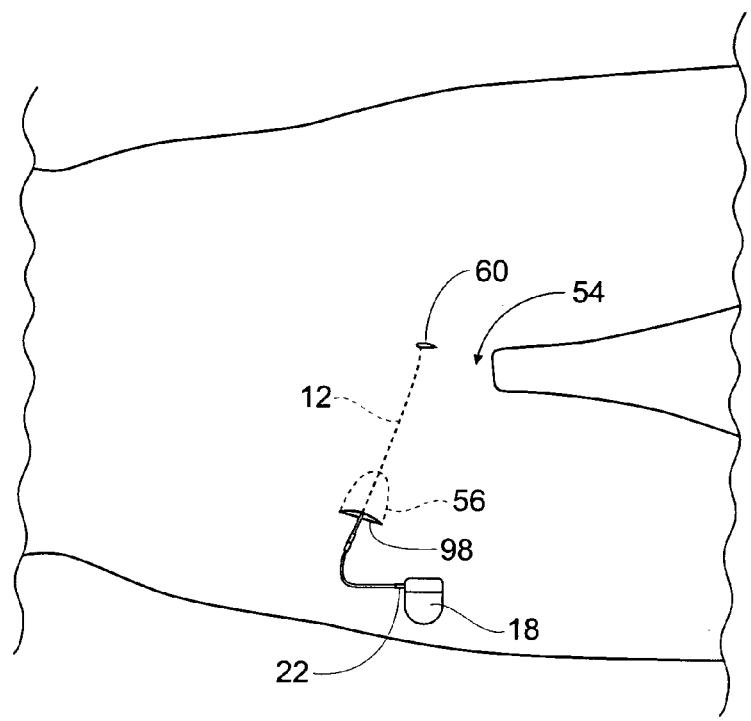

Having developed the subcutaneous pocket 56 for the implantable pulse generator 18, a subcutaneous tunnel is formed for connecting the electrode 16 to the implantable pulse generator 18. First (as FIG. 15 shows), the size of the needle puncture site 60 is increased using a skin knife. Next, the tunneling tool 40 (shown in FIG. 2) is passed through the pocket incision site 98 (see FIG. 16) toward and through the needle puncture site 60. The tunneling tool 40 desirably includes a removable blunt tip 62 (see FIG. 2) that is present during tunneling, but that is removed once passage through the distant incision site 60 occurs. With the blunt tip 62 removed, the lead 12 can be passed through the open lumen of the tunneling tool 40 to the pocket incision site 98, as FIG. 17 shows. Withdrawal of the tunneling tool 40 delivers the plug 22 of the lead 12 through the pocket incision 98 into the procedural field.

It should be appreciated that, in an alternative technique, a tunneling tool 40 comprising a stylet and sheath can be placed at the site of the needle puncture site and advanced toward the pocket incision. Removal of the stylet allows the physician to pass the lead 12 through the sheath to the pocket incision site, followed by removal of the sheath.

Connecting the Lead to the Implicatable Pulse Generator

Once the lead 12 has been tunneled to the pocket incision site (see FIG. 18), the plug 22 can be connected to the implantable pulse generator 18.

Implanting the Implantable Pulse Generator

Figure 19:
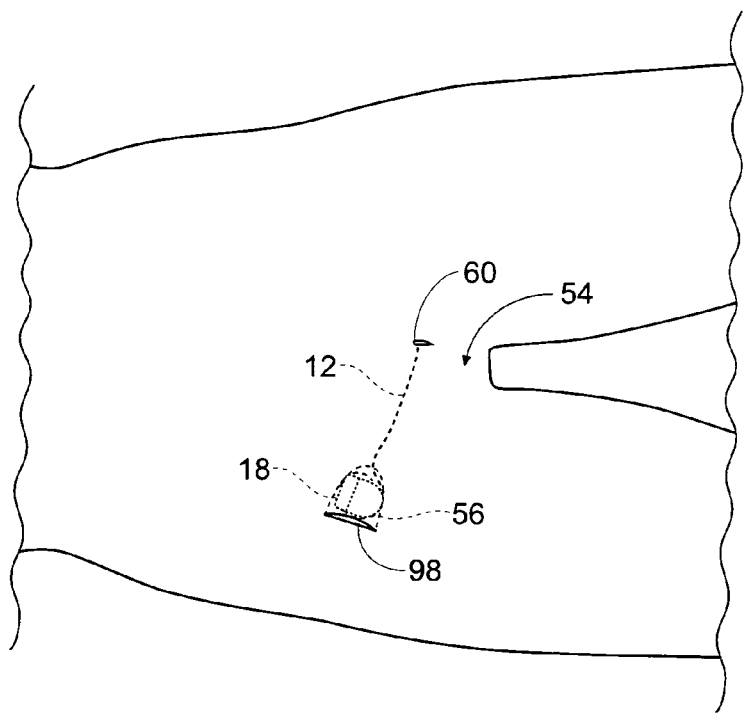

Once the lead 12 has been connected to the implantable pulse generator 18, the lead 12 and implanrable pulse generator can be placed into the pocket 56 (as FIG. 19 shows). The implantable pulse generator 18 is located approximately 1 cm from the surface of the skin; and the cable is oriented with an open loop of cable to allow for motion of the abdominal contents without transmitting forces along the cable and lead.

Figure 20:
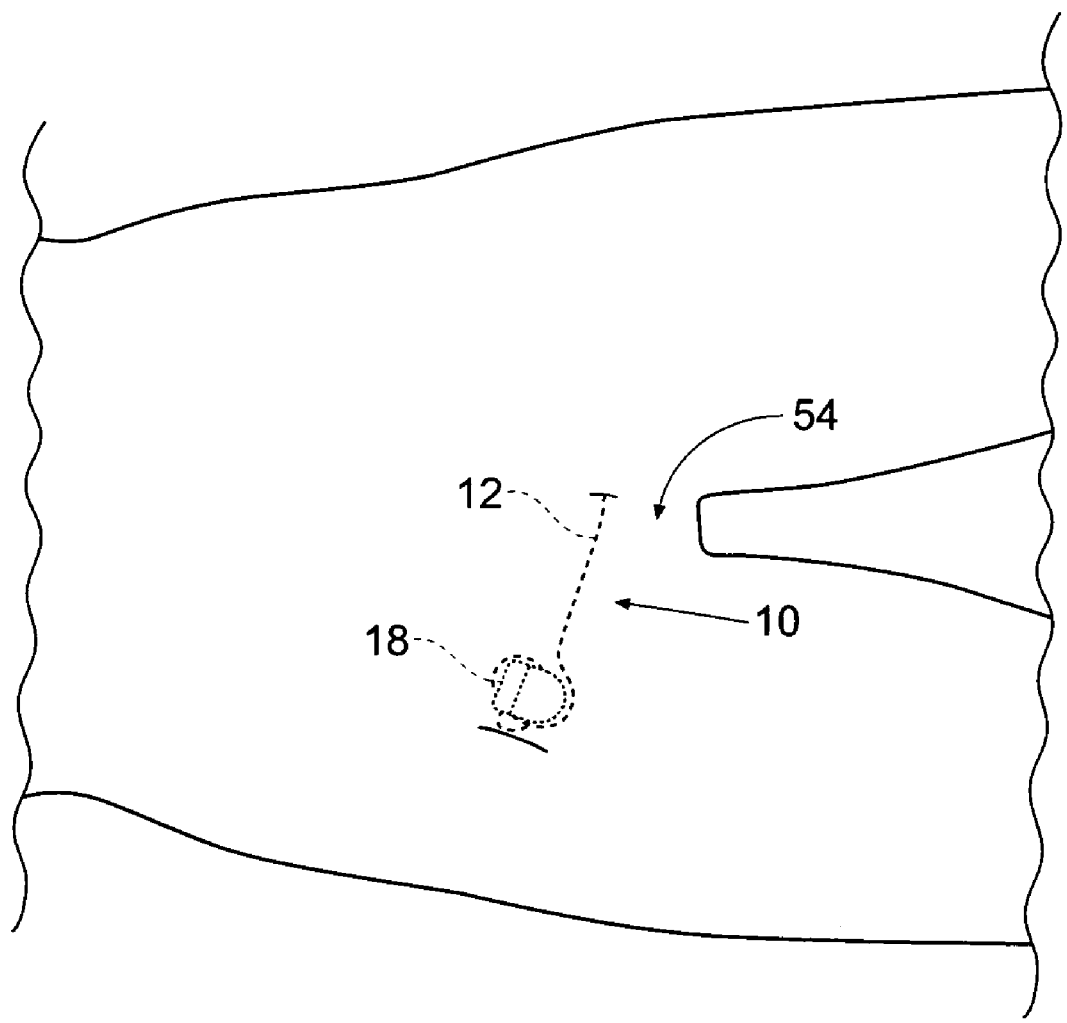
Figure 21:
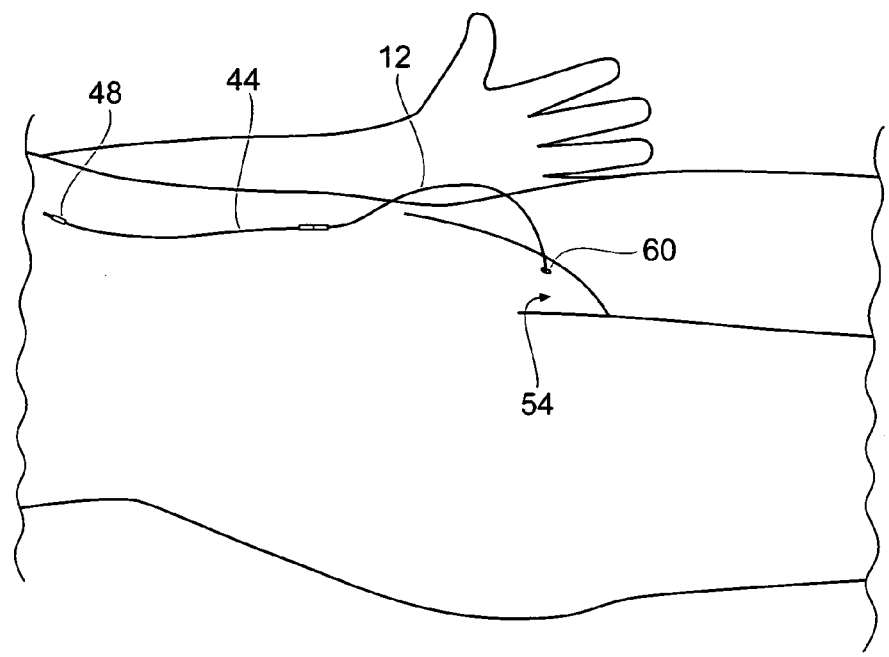
FIGS. 21 to 30 illustrate steps of implanting the system shown in FIG. 1 in a two stage surgical procedure.

Both wound sites are irrigated with irrigation solutions (½ strength betadine or Hibiclens solution or equivalent). The skin sites are closed using Derma-bond glue or stitches of 4-0 vicryl, as FIG. 20 shows. Dressing is desirably applied for about twenty-four hours. The incisions are desirably kept dry for forty-eight hours.

2. Two Stage Surgical Procedure

FIGS. 21 to 30 illustrate steps of implanting an implant system 10 in a two stage surgical procedure. As before described, the first stage installs the electrode 16 and lead 12 in the manner described above, and connects the lead 12 to a temporary external pulse generator 34. If the use of the external pulse generator 34 achieves the desired results, an implantable pulse generator is implanted in the second stage in the manner described above.

a. The First Stage

Figure 3:
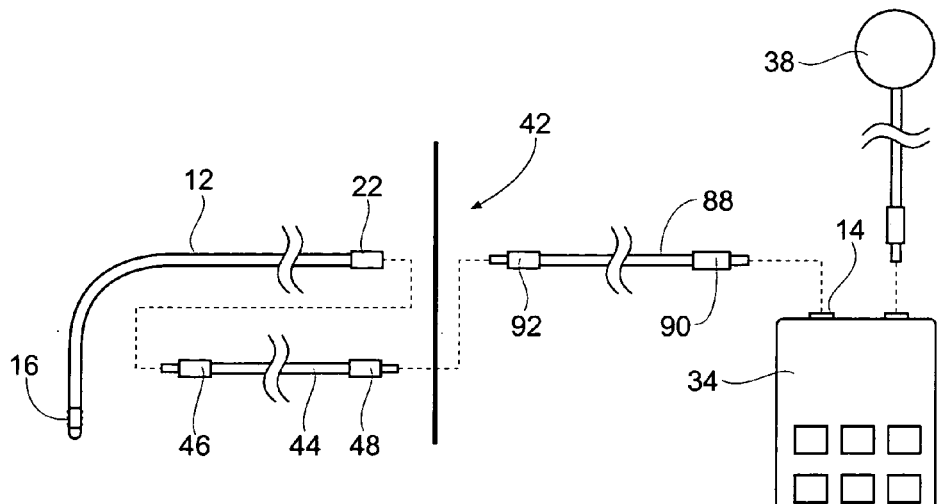
FIG. 3 is a plane view of test screening system that can used when the system shown in FIG. 1 is implanted in a two stage surgical procedure.

Tunneling the Lead and Percutaneous Extension Cable for Connection to an External Pulse Generator The same preoperative antibiotics and skin prep as previously described are performed. Under anesthesia, the electrode 16/lead 12 are located and tunneled to the site that will later (in stage 2) hold the implantable pulse generator. In the first stage (see FIG. 21), the lead 12 is connected to the percutaneous extension cable 44, which has been earlier described and is shown in FIG. 3.

Figure 22:
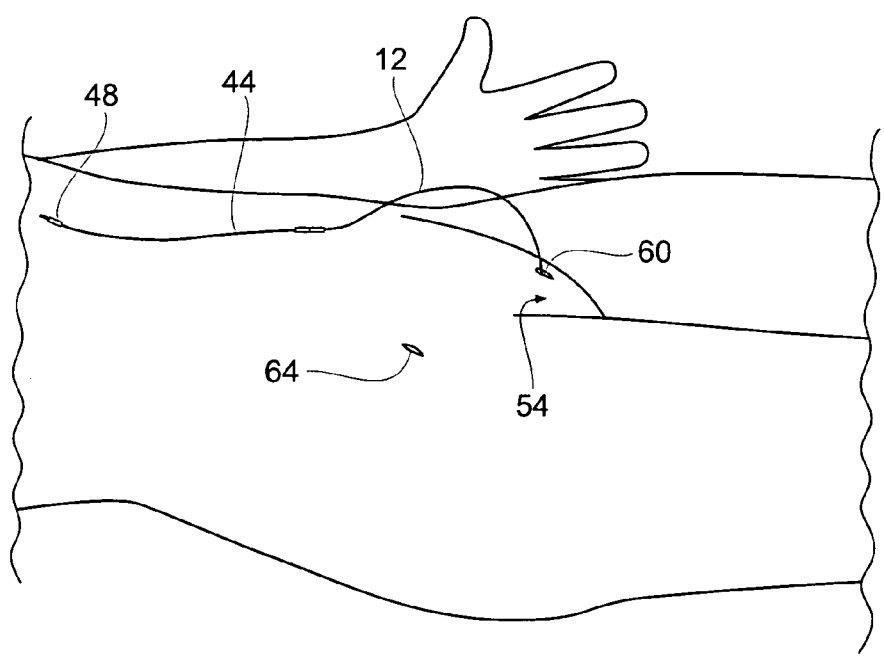

After placement of the electrode 16/lead 12 and the connection of the percutaneous extension cable 44, as FIG. 22 shows, under anesthesia, a first incision 64 is formed at the intended site of the pocket 56 for the implantable pulse generator 18. As before described, this site 64 is generally located two finger-breaths medial to the anterior iliac spine and made in the direction of the dermatomal skin line. The size of the needle puncture site 60 is also increased using a skin knife, in preparation for tunneling.

Figure 23:
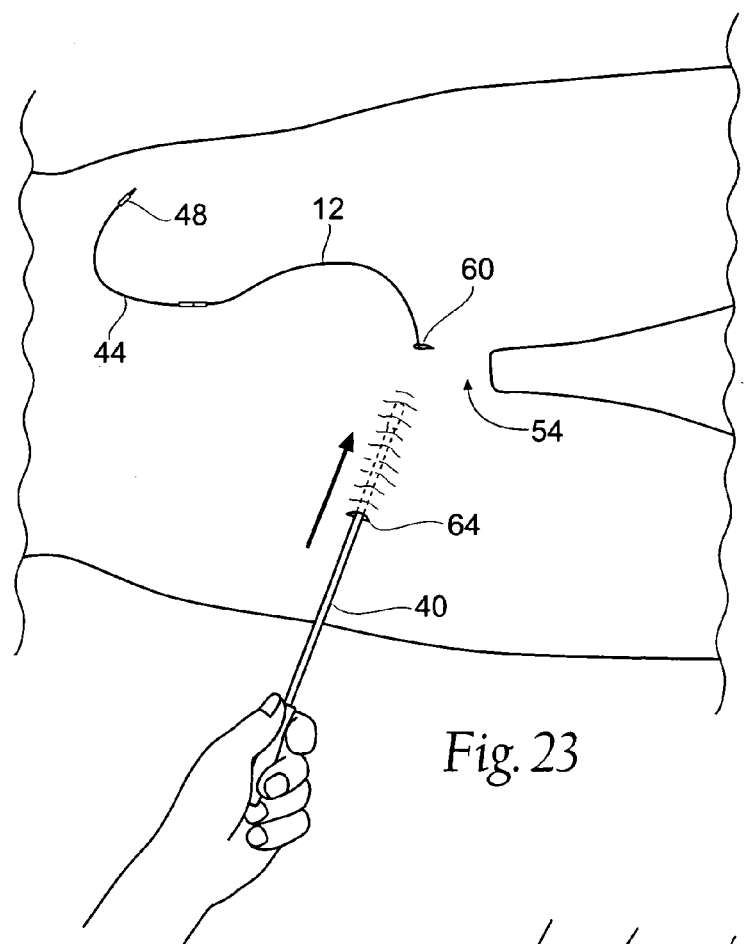
Figure 24:
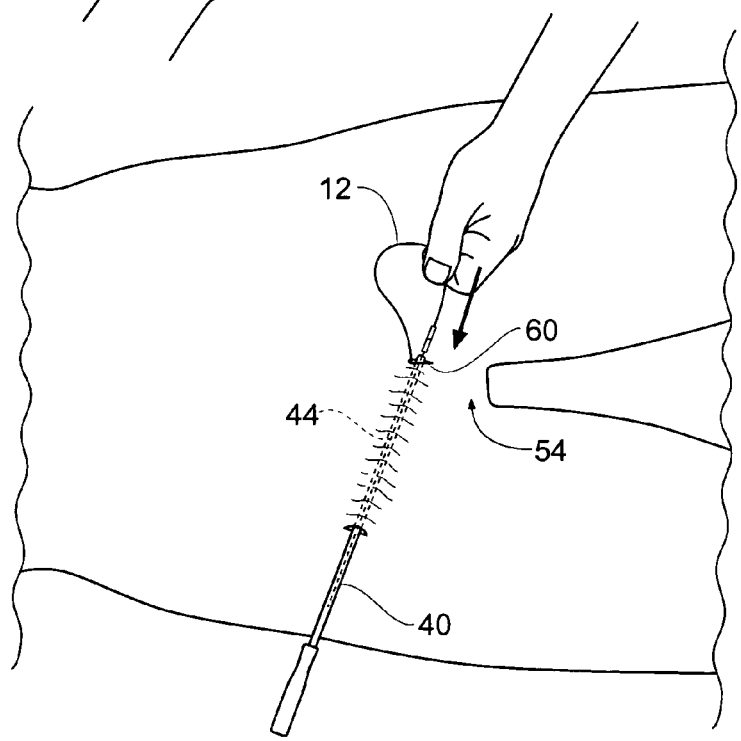

As FIG. 23 shows, a tunneling tool 40 (shown in FIG. 2) is passed through the first incision 64 toward and through the needle puncture site 60 (or vice versa), as previously described. The blunt tip 62 of the tunneling tool 40 is removed, and the percutaneous extension cable 44 and connected lead 12 are passed through the open lumen of the tunneling tool 40 to the first incision site 64. Withdrawal of the tunneling tool 40 delivers the plug 48 of the percutaneous extension cable 44 through the first incision 64 into the procedural field.

Figure 25:
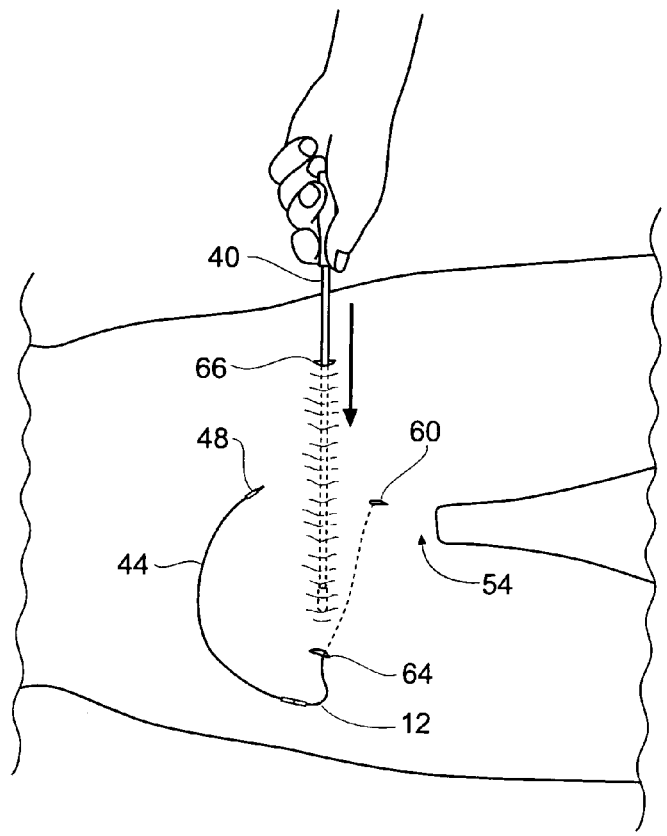

As FIG. 25 shows, a second incision site 66 is made across the pelvis away from the first incision site 64. The percutaneous extension cable 44 will be eventually routed to the second incision site 66. In this way, should infection occur in the region where the percutaneous extension cable 44 extends from the skin, the infection occurs away from the region where the pocket 56 for the implantable pulse generator 18 is to be formed (i.e., at the first incision site 64). The first incision site 64 is thereby shielded from channel infection during the first stage, in anticipation forming a stetile pocket 56 for the implantable generator in the second stage.

Figure 26:
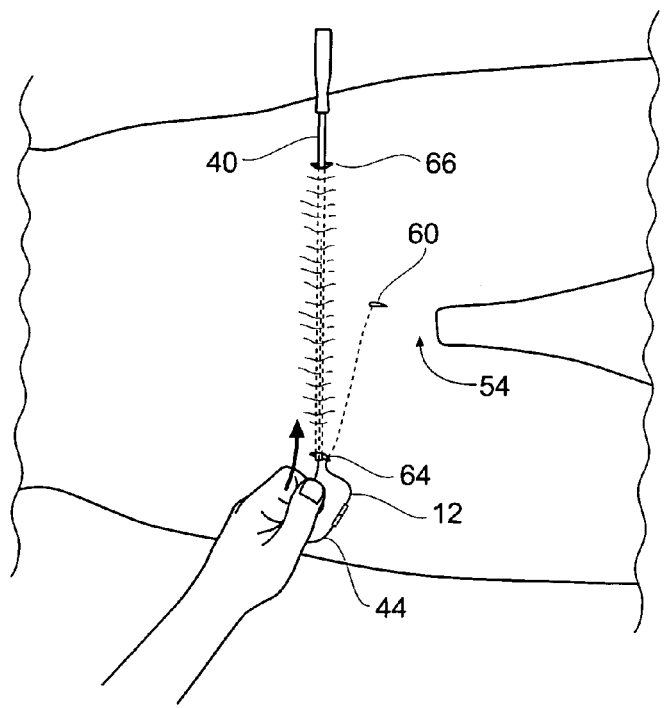
Figure 27:
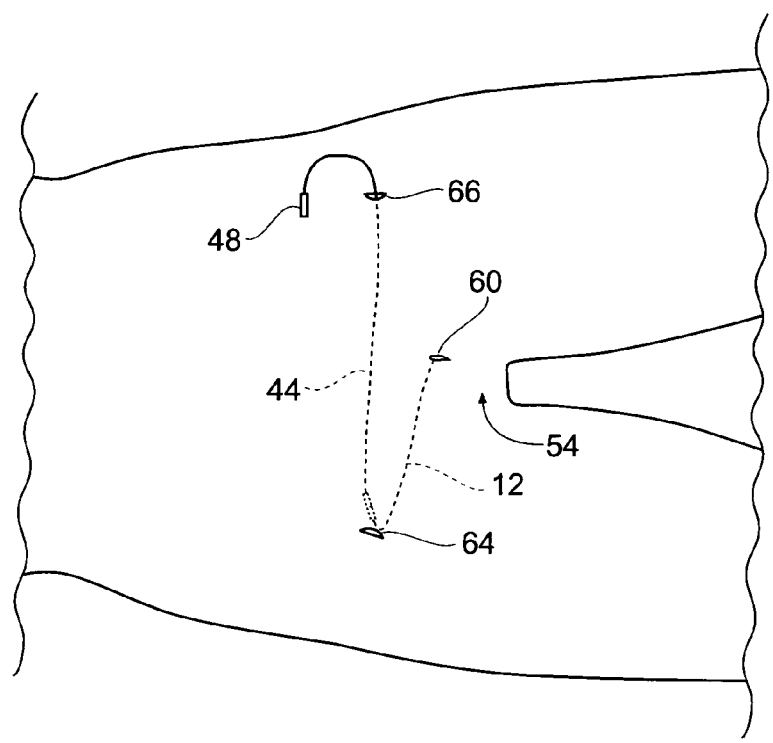
Figure 28:
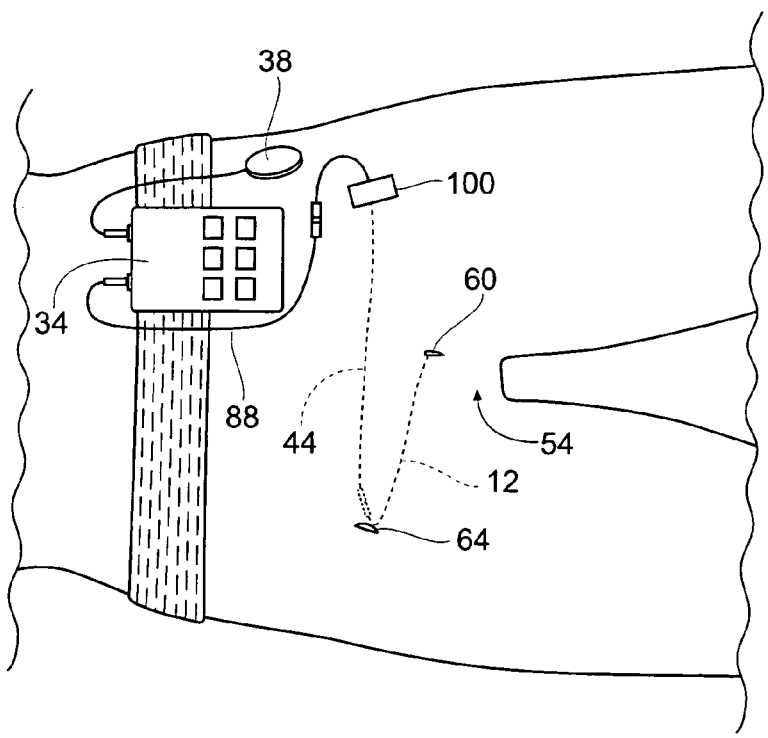

More particularly, the tunneling tool 40 is advanced from the second incision site 66 subcutaneously toward and through the first incision site 64 (or vice versa). As FIG. 26 shows, the blunt tip 62 of the tunneling tool 40 is removed, and the percutaneous extension cable 44 is passed through the open lumen of the tunneling tool 40 to the second incision site. Withdrawal of the tunneling tool 40 (see FIG. 27) delivers the plug 48 of the percutaneous extension cable 44 through the second incision 66 into the procedural field. A short length of the percutaneous cable 44 is then secured externally to the skin with sterile tape 100. At this point the plug 48 at the end of the percutaneous extension cable 44 is available for connection to the external test cable 88 (as FIG. 28 shows). The remainder of the percutaneous cable 44 is located under the skin and is free of exposure to outside contamination. The sterile tape 100 covering the exit site and the re-growth of tissue maintains this sterile barrier.

All wound sites are irrigated with irrigation solutions and closed using Derma-bond glue or stitches of 4-0 vicryl, as FIG. 28 shows.

An external pulse generator 34 of the type previously described is coupled to the exposed plug 48 of the percutaneous extension cable through an external test cable 88, as FIG. 28 shows. The patch electrode 38 is placed on the skin and likewise coupled to the external pulse generator 34. The individual wears the external pulse generator 34 (e.g., in a belt holster or taped to the skin) and return patch electrode 38 (on the skin) for the prescribed test period. The external pulse generator 34 supplies the prescribed stimulation regime. If an improvement in urinary continence is achieved during the test phase, the second phase of the surgical procedure is scheduled to proceed.

Figure 42:
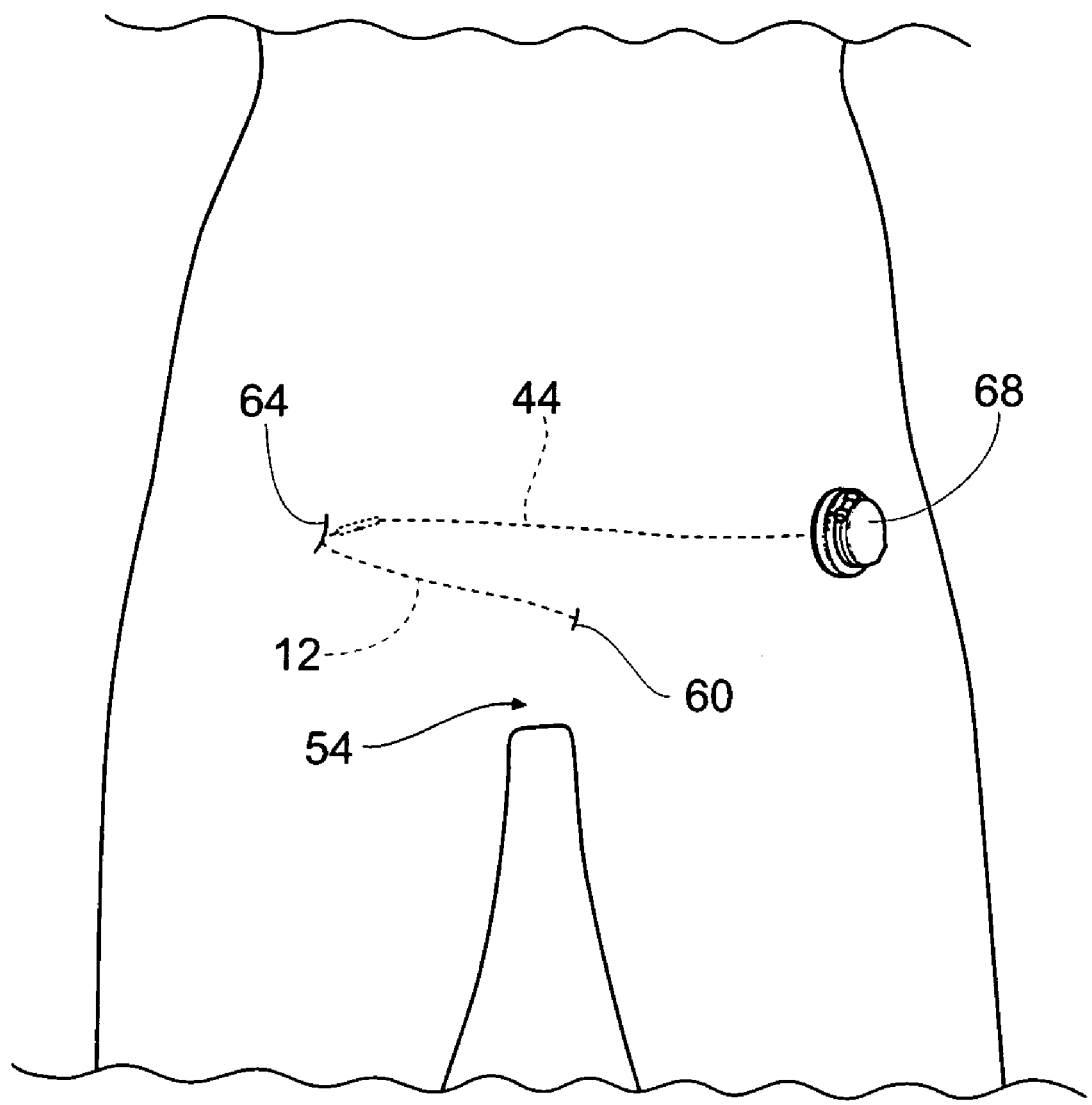
FIG. 42 is an anterior anatomic view of an embodiment of an external pulse generator coupled to a lead and electrode during the test stage of a two step surgical procedure for implanting the system shown in FIG. 1.

Instead of using an external pulse generator 34 as shown in FIG. 28, a neuromuscular stimulation device 68 can be used of the type described in co-pending U.S. Pat. application Ser. No. 10/777,771, filed Feb. 12, 2004 and entitled "Portable Percutaneous Assemblies, Systems, and Methods for Providing Highly Selective Functional or Therapeutic Neurostimulation," which is incorporated herein by reference. As shown in FIG. 42, the device 68 comprises a skin-worn patch or carrier, which can be carried, e.g., by use of a pressure-sensitive adhesive, without discomfort and without affecting body image on the torso of an individual near the second incision. The carrier carries an on-board electronics pod, which generates the desired electrical current patterns. The pod houses microprocessor-based, programmable circuitry that generates stimulus currents, time or sequence stimulation pulses, and logs and monitors usage. The electronics pod also includes an electrode connection region, to physically and electrically couple the lead 12 to the circuitry of the electronics pod. The carrier also includes a power input bay, to receive a small, lightweight, primary cell battery, which can be released and replaced as prescribed. The battery provides power to the electronics pod. It is contemplated that, in a typical regime during stage one, the individual will be instructed to regularly remove and discard the battery (e.g., about once a day or once a week), replacing it with a fresh battery. This arrangement simplifies meeting the power demands of the electronics pod. The use of the neuromuscular stimulation device parallels a normal, accustomed medication regime, with the battery being replaced at a prescribed frequency similar to an individual administering a medication regime in pill form.

b. The Second Stage Removing the Percutaneous Extension Cable

Figure 29:
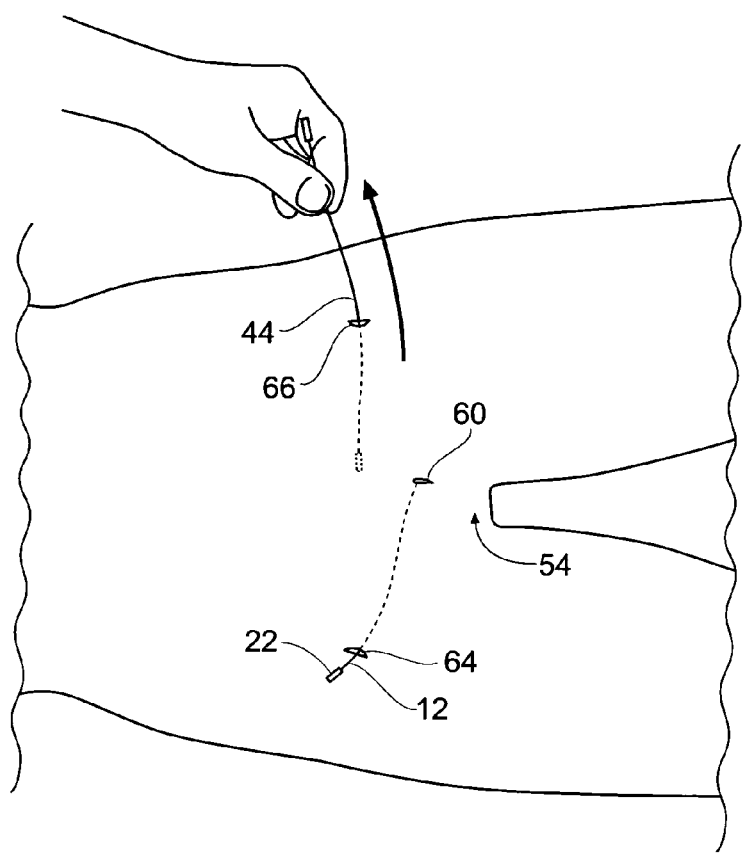

The same preoperative antibiotics and skin prep as previously described are performed. In the second stage, the external pulse generator 34, return electrode 38, and external test cable 88 are disconnected from the percutaneous extension cable 44. As shown in FIG. 29, under local anesthesia, the first and second incisions 64 and 66 are reopened. The connection between the percutaneous extension cable 44 and lead 12 is disconnected. The percutaneous extension cable 44 is removed through the second incision 66 and discarded, as FIG. 29 shows.

Forming the Implantable Pulse Generator Pocket

Figure 30:
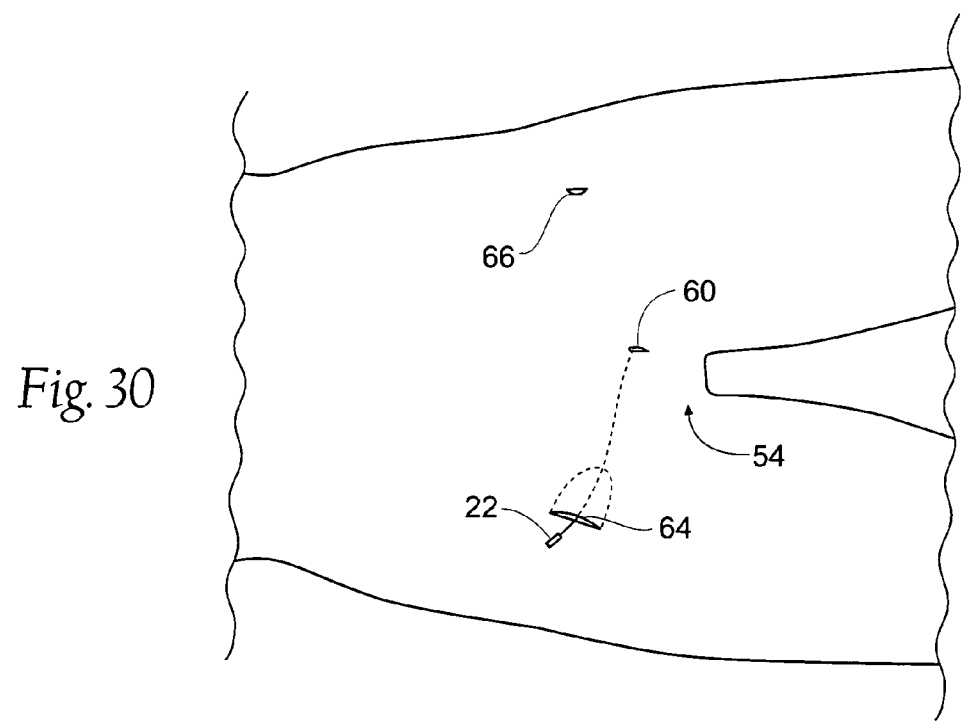

Following removal of the percutaneous extension cable 44, the first incision 64 is enlarged to form a subcutaneous pocket 56 to accept the implantable pulse generator 18 using blunt dissection techniques of the subcutaneous tissues, as previously described (see FIG. 30). The connector 14 of the lead 12 is extracted through the pocket 56 into the procedural field.

Connecting the Lead to the Implantable Pulse Generator

With the pocket 56 formed (see FIG. 18), and the lead 12 delivered into the procedural field, the lead can now be connected to the implantable pulse generator 18.

Implanting the Implantable Pulse Generator

Once the lead 12 has been connected to the implantable pulse generator 18, the lead 12 and implantable pulse generator can be placed into the pocket 56 (as FIG. 19 shows). The implantable pulse generator is located approximately 1 cm from the surface of the skin; and the cable is oriented with an open loop of cable to allow for motion of the abdominal contents without transmitting forces along the cable and lead.

The wound sites (first and second incisions) are irrigated with irrigation solutions (1/2 strength betadine or Hibiclens solution). The skin sites are closed using Derma-bond glue or stitches of 4-0 vicryl, as FIG. 20 shows.

Dressing is desirably applied for about twenty-four hours. The incisions are desirably kept dry for forty-eight hours.

III. Features of the Lead and Electrode

A. Implantation in Adipose Tissue

Neurostimulation leads and electrodes that may be well suited for implantation in muscle tissue are not well not suited for implantation in soft adipose tissue 54 in the targeted location at or near the pubic symphysis. This is because adipose tissue 54 is unlike muscle tissue, and also because the vascularization and innervation of tissue at or near the pubic symphysis is unlike tissue in a muscle mass. Muscular tissue is formed by tough bundles of fibers with intermediate areolar tissue. The fibers consist of a contractile substance enclosed in a tubular sheath. The fibers lend bulk, density, and strength to muscle tissue that are not found in soft adipose tissue 54. Muscles are also not innervated with sensory nerves or highly vascularized with blood vessels to the extent found in the pubic region of the body.

Figure 33:
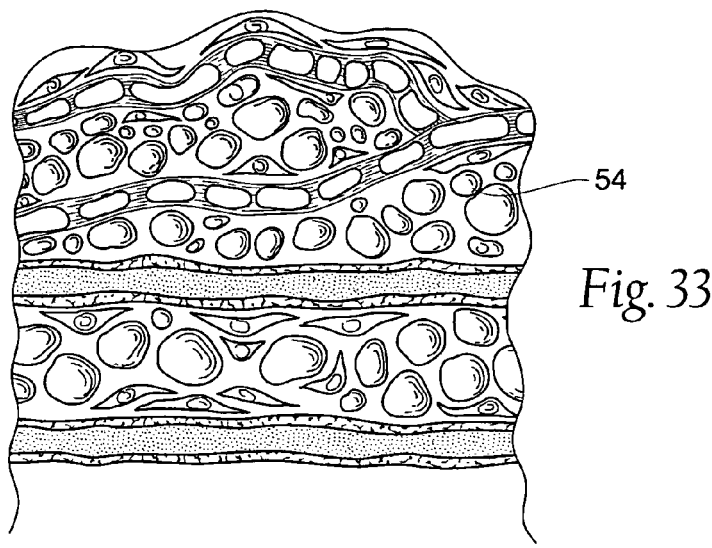
FIG. 33 is an anatomic section view of a region of adipose tissue.

Adipose tissue 54 (see FIG. 33) consists of small vesicles, called fat-cells, lodged in the meshes of highly vascularized areolar tissue containing minute veins, minute arteries, and capillary blood vessels. The fat-cells vary in size, but are about the average diameter of 1/500 of an inch. They are formed of an exceedingly delicate protoplasmic membrane, filled with fatty matter, which is liquid during life and turns solid after death. They are round or spherical where they have not been subject to pressure; otherwise they assume a more or less angular outline. The fat-cells are contained in clusters in the areolae of fine connective tissue, and are held together mainly by a network of capillary blood vessels, which are distributed to them.

Figure 34:
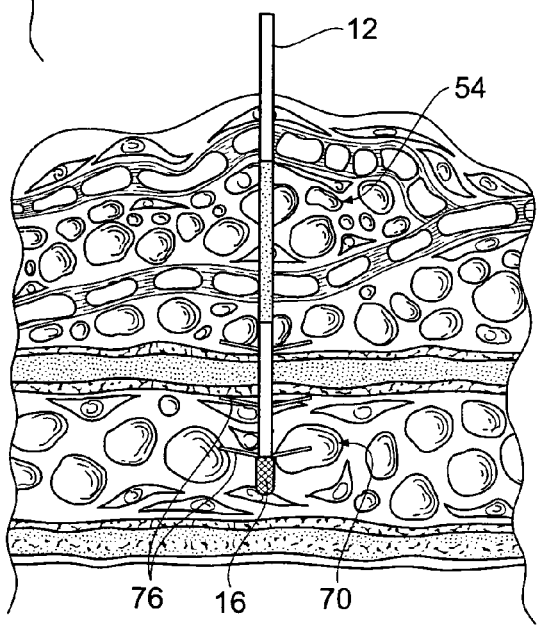
FIGS. 34 and 35 are anatomic section views of the adipose tissue region shown in FIG. 33 with a single lead and electrode associated with the system shown in FIG. 1, after having been implanted.

The lead 12 and electrode 16 are sized and configured to be inserted into and to rest in soft adipose tissue 54 (see FIG. 34) in the lower abdomen without causing pain or discomfort or impact body image. Desirably, the lead 12 and electrode 16 can be inserted using a small (e.g., smaller than 16 gauge) introducer with minimal tissue trauma. The lead 12 and electrode 16 are formed from a biocompatible and electrochemically suitable material and possess no sharp features that can irritate tissue during extended use. Furthermore, the lead 12 and electrode 16 possess mechanical characteristics including mechanical compliance (flexibility) along their axis (axially), as well as perpendicular to their axis (radially), and unable to transmit torque, to flexibly respond to dynamic stretching, bending, and crushing forces that can be encountered within soft, mobile adipose tissue 54 in this body region without damage or breakage, and to accommodate relative movement of the implantable pulse generator coupled to the lead 12 without imposing force or torque to the electrode 16 which tends to dislodge the electrode.

Furthermore, the lead 12 and electrode 16 desirably include an anchoring means 70 for providing retention strength to resist migration within or extrusion from soft, mobile adipose tissue 54 in this body region in response to force conditions normally encountered during periods of extended use. In addition, the anchoring means 70 is desirably sized and configured to permit the electrode 16 position to be adjusted easily during insertion, allowing placement at the optimal location where bilateral stimulation of the left and right branches of the genital nerves occurs. The anchoring means 70 functions to hold the electrode at the implanted location despite the motion of the tissue and small forces transmitted by the lead due to relative motion of the connected implantable pulse generator due to changes in body posture or external forces applied to the abdomen. However, the anchoring means 70 should allow reliable release of the electrode 16 at higher force levels, to permit withdrawal of the implanted electrode 16 by purposeful pulling on the lead 12 at such higher force levels, without breaking or leaving fragments, should removal of the implanted electrode 16 be desired.

B. The Lead

Figure 36:
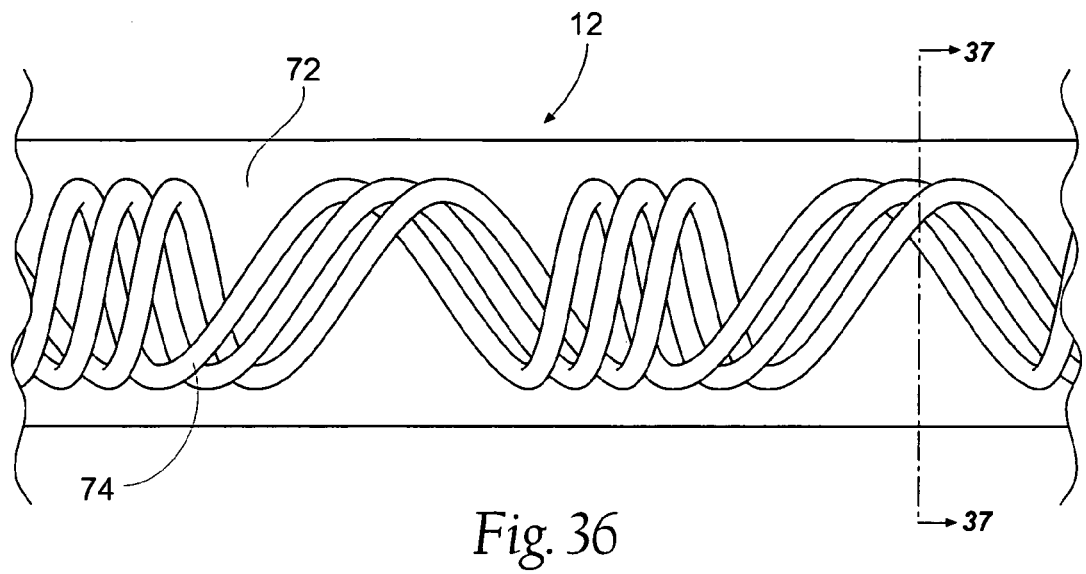
FIG. 36 is a side interior view of a representative embodiment of a lead of the type shown in FIGS. 34 and 35.
Figure 37:
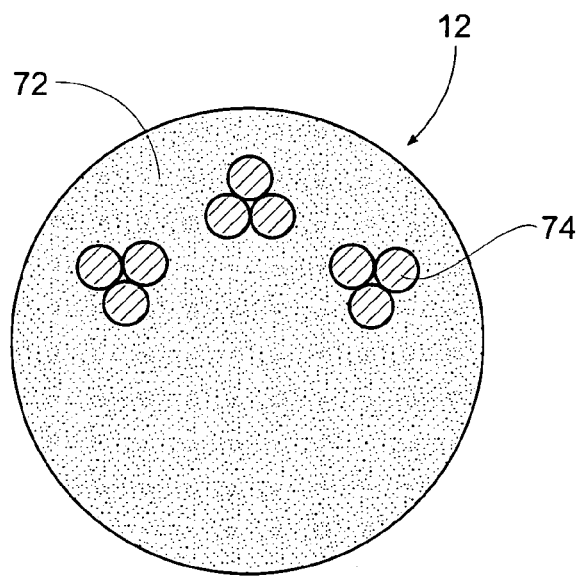
FIG. 37 is an end section view of the lead taken generally along line 37-37 in FIG. 36.

FIGS. 36 and 37 show a representative embodiment of a lead 12 and electrode 16 that provide the foregoing features. The lead 12 comprises a molded or extruded component 72, which encapsulates a coiled stranded wire element 74. The wire element may be bifilar, as shown in FIG. 36. The molded or extruded lead 12 can have an outside diameter as small as about 1 mm. The lead 12 may be approximately 10 cm to 30 cm in length.

The coil's pitch can be constant or, as FIG. 36 shows, the coil's pitch can alternate from high to low spacing to allow for flexibility in both compression and tension. The tight pitch will allow for movement in tension, while the open pitch will allow for movement in compression.

C. The Electrode

The electrode 16 or electrically conductive surface can be formed from Pair (or, alternatively, 316L stainless steel) and possess a conductive surface of approximately 10 mm²-20 mm². This surface area provides current densities up to 2mA/mm2 with per pulse charge densities less than 0.5 µC/mm2.

Figure 35:
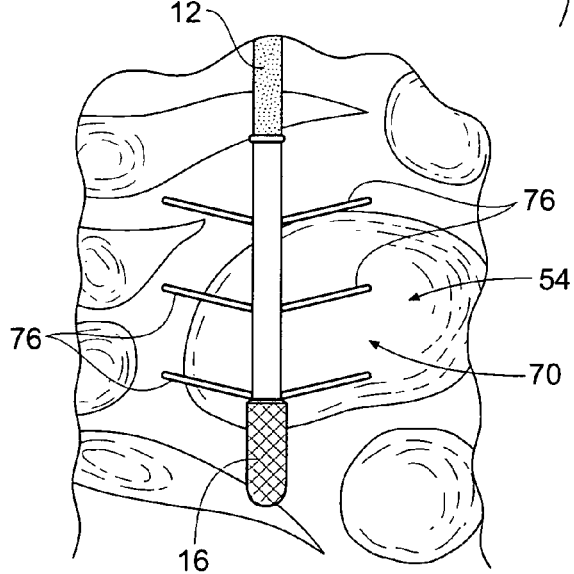

FIG. 35 shows a monopolar electrode configuration. In use, the casing of the implantable pulse generator 18 serves as a return electrode. In the monopolar electrode arrangement, the single electrode 16 is provided at the distal-most end.

Alternatively, one or more additional conductive surfaces can be provided, spaced proximally from the tip electrode 16, to provide a bipolar electrode configuration.

D. The Anchoring Means

In the illustrated embodiment (see FIG. 38B), the anchoring means 70 takes the form of an array of flexible tines 76 or filaments proximal to the distal-most electrode 16. The tines 76 are desirably present relatively large, planar surfaces, and are placed in multiple rows axially along the lead 12. The tines 76 are normally biased toward a radially outward condition into tissue. In this condition, the large surface area and orientation of the tines 76 allow the lead 12 to resist dislodgement or migration of the electrode 16 out of the correct location in the surrounding tissue. In the illustrated embodiment, the tines 76 are biased toward a proximal-pointing orientation, to better resist proximal migration of the electrode 16 with lead tension. The tines 76 are desirably made from a polymer material, e.g., high durometer silicone, polyurethane, or polypropylene, bonded to or molded with the lead 12.

The tines 76 can be deflected toward a distal direction in response to exerting a pulling force on the lead 12 at a threshold axial force level, which is greater than expected day-to-day axial forces. The tines 76 are sized and configured to yield during proximal passage through tissue in result to such forces, causing minimal tissue trauma, and without breaking or leaving fragments, despite the possible presence of some degree of tissue in-growth. This feature permits the withdrawal of the implanted electrode 16, if desired, by purposeful pulling on the lead 12 at the higher axial force level.

Desirably, the anchoring means 70 is prevented from fully engaging body tissue until after the electrode 16 has been deployed. The electrode 16 is not deployed until after it has been correctly located during the implantation (installation) process.

Figure 38A:
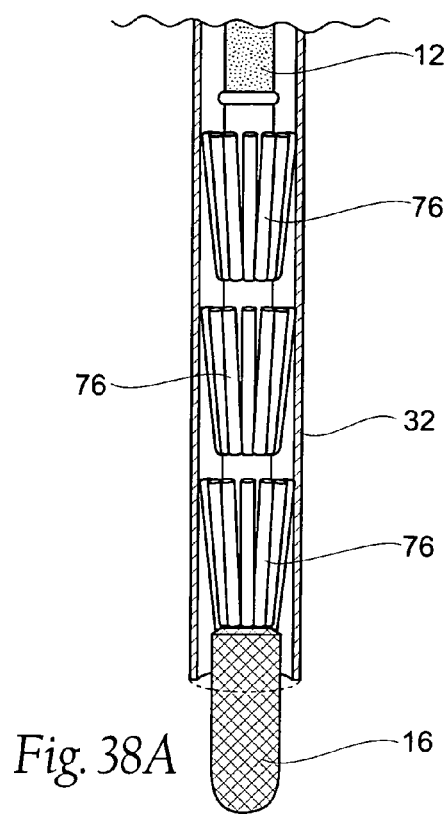
FIG. 38A is an elevation view, in section, of a lead and electrode of the type shown in FIGS. 34 and 35 residing within an introducer sheath for implantation in a targeted tissue region, the anchoring members being shown retracted within the sheath.
Figure 38B:
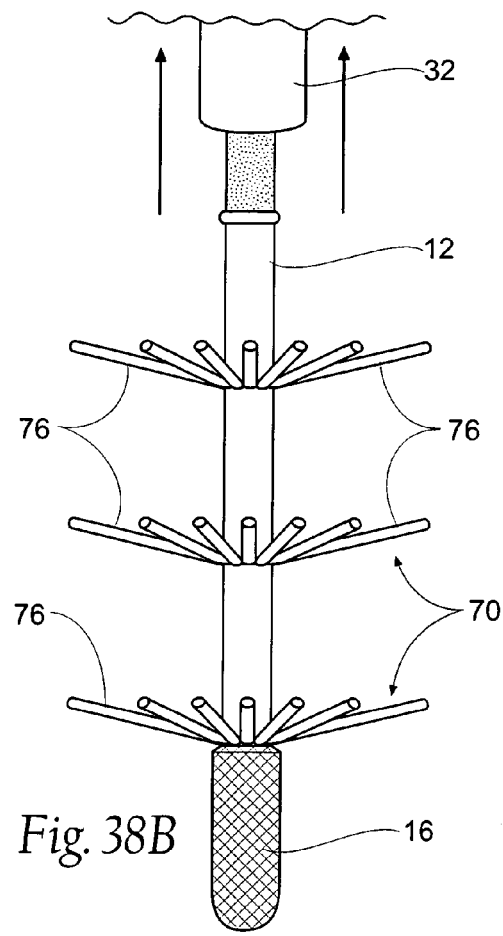
FIG. 38B is an elevation view, in section, of a lead and electrode of the type shown in FIG. 39 after withdrawal of the introducer sheath 32, the anchoring members being shown extended for use.

More particularly, as before described, the lead 12 and electrode 16 are intended to be percutaneously introduced through a sleeve 32 shown in FIG. 2 (this is also shown in FIG. 12). As shown in FIG. 38A, the tines 76 assume a collapsed condition against the lead 12 body when within the sleeve 32. In this condition, the tines 76 are shielded from contact with tissue. Once the location is found, the sleeve 32 can be withdrawn, holding the lead 12 and electrode 16 stationary (see FIG. 38B. Free of the sleeve 32, the tines 76 spring open to assume their radially deployed condition in tissue, fixing the electrode 16 in the desired location.

The position of the electrode 16 relative to the anchoring means 70, and the use of the sleeve 32, allows for both advancement and retraction of the electrode delivery sleeve during implantation while simultaneously delivering test stimulation. The sleeve 32 can be drawn back relative to the lead 12 to deploy the electrode 16 anchoring means 70, but only when the physician determines that the desired electrode location has been reached. The withdrawal of the sleeve 32 from the lead 12 causes the anchoring means 70 to deploy without changing the position of electrode 16 in the desired location (or allowing only a small and predictable, set motion of the electrode). Once the sleeve 32 is removed, the flexible, silicone-coated or polyurethane-coat lead 12 and electrode 16 are left implanted in the tissue.

Figure 39:
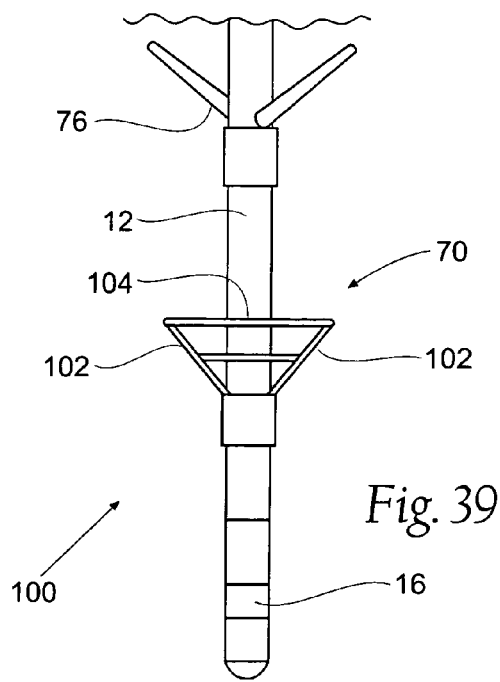
FIG. 39 is an elevation view of an alternative representative embodiment of lead having anchoring members.

As shown in FIG. 39, the anchoring means 70 can include an open-form conical structure 100 proximal to the distal-most electrode 16, alone or in combination with one or more arrays of flexible tines 76 spaced more proximally away from the electrode. In the illustrated embodiment, the structure 100 comprises an array of circumferentially spaced-apart tines 102 joined by cross members 104, thereby forming a conically shaped basket structure that increases in diameter (i.e., by tapering radially outward) with distance from the electrode 12. The tines 102 and cross members 104 are desirably made from flexible or resilient wire or polymer material, so that the structure 100 can be collapsed back against the lead 12 into a low profile for introduction through the sleeve 32. Withdrawal of the sleeve 32 frees the structure 100 to resiliendy spring into the open-form conical shape shown in FIG. 39. The structure 100 provides localized stabilization for the more distal regions of the lead 12, including the electrode 16, which is additive to the stabilization provided to the more proximal regions of the lead 12 by the more proximally spaced tines 76. Together, the structure 100 and the tines 76 provide complementary ("belt-and-suspenders") resistance against migration of the lead 12 and electrode 16 within mobile adipose tissue 54 in response to forces that tend to flex or twist the more distal regions of the lead 12 relative to more proximal regions of the lead 12.

IV. Kits

Figure 40:
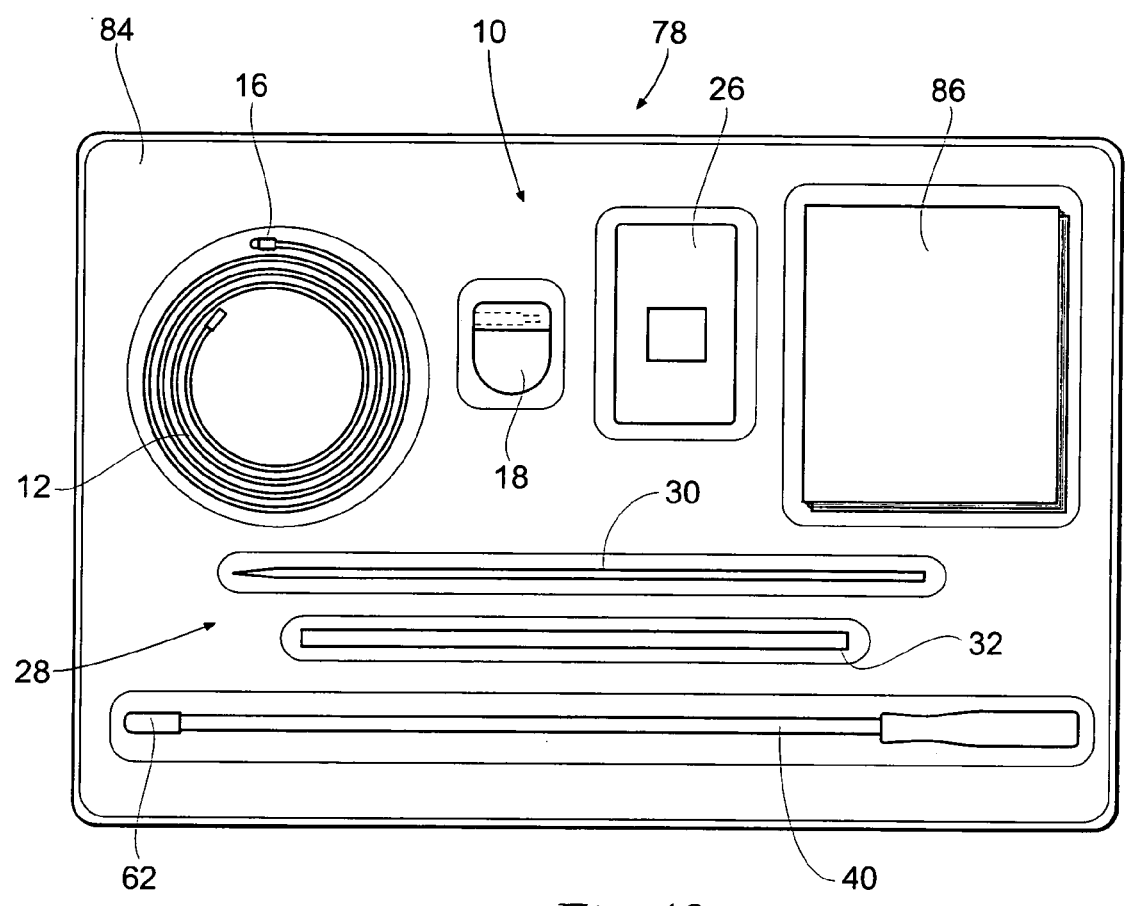
FIG. 40 is a plane view of a kit packaging the implant system shown in FIG. 1 for use.
Figure 41:
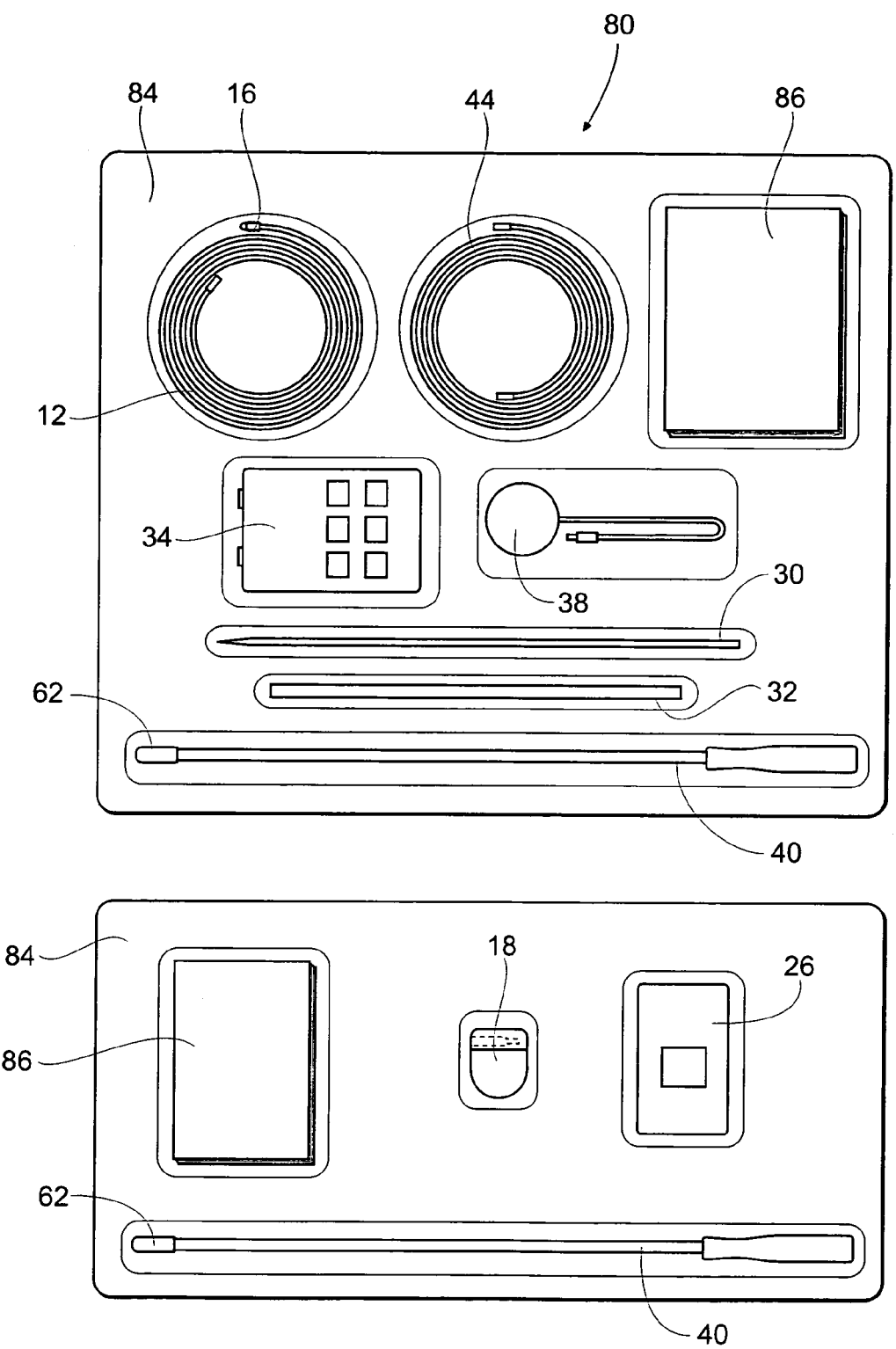
FIG. 41 is a plane view of two kits that facilitate the implantation of an implant system shown in FIG. 1 in a two stage surgical procedure.

As FIGS. 40 and 41 show, the various tools and devices as just described can be consolidated for use in functional kits 78, 80, and 82. The kits 78, 80, and 82 can take various forms. In the illustrated embodiment, each kit 78, 80, and 82 comprises a sterile, wrapped assembly. Each kit 78, 80, and 82 includes an interior tray 84 made, e.g., from die cut cardboard, plastic sheet, or thermo-formed plastic material, which hold the contents. Each kit 78, 80, and 82 also preferably includes directions 86 for using the contents of the kit to carry out a desired procedure.

The directions 86 can, of course vary. The directions 86 shall be physically present in the kits, but can also be supplied separately. The directions 86 can be embodied in separate instruction manuals, or in video or audio tapes, CD's, and DVD's. The instructions 86 for use can also be available through an internet web page.

The arrangement and contents of the kits 78, 80, and 82 can vary.

For example, in FIG. 40, a representative kit 78 is shown for carrying out a single stage implant procedure as previously described. The kit 78 includes the implant system 10 comprising the implantable lead 12 and electrode 16, an implantable pulse generator 18, and an external controller 26. The kit 78 also includes the surgical tool system 28 comprising the needle 30, sleeve 32, and tunneling tool 40. An external pulse generator 34 can also be provided, but this device will typically be available in the surgical suite. The instructions 86 for use in the kit 78 direct use of these instruments to implant the lead 12 and electrode 16, form the subcutaneous pocket, tunnel the lead 12, and implant the implantable pulse generator 18 in the subcutaneous pocket in the manner previously described and as shown in FIGS. 9 to 20. The instructions 86 for use can also direct use of the external controller 26 to operate the implantable pulse generator 18, as well as use of a clinician programmer 52 to program the implantable pulse generator 18.

As another example, in FIG. 41, two representative kits 80 and 82 are shown that, together, allow the physician to carry out a two stage surgical procedure. The first kit 80 includes the test screening system 42 comprising the implantable lead 12 and electrode 16, the percutaneous extension cable 44, and an external pulse generator 34 and patch electrode 38 for use on a temporary basis during the screening phase. The kit 80 also includes the surgical tools system comprising the needle 30, sleeve 32, and tunneling tool 40. The instructions 86 for use direct use of these instruments to install the lead 12 and electrode 16, tunnel the lead 12 and percutaneous cable 44, and connect the temporary external pulse generator 34 during a first surgical stage for patient screening purposes, in the manner previously described and as shown in FIGS. 21 to 27. The instructions 86 for use can also direct use of the external pulse generator 34.

The second kit 82 contains the instruments to carry out the second stage of the procedure. The second kit 82 includes an implantable pulse generator 18, an external controller 26, and a tunneling tool 40. The instructions 86 for use direct use of these components to remove the percutaneous cable 44 and couple the lead 12 to the implantable pulse generator 18, and implant the implantable pulse generator 18 in a subcutaneous pocket in the manner previously described and as shown in FIGS. 28 to 30 and 18 to 20. The instructions 86 for use can also direct use of the external controller 26 to operate the implantable pulse generator, as well as use of a clinician programmer to program the implantable pulse generator.

Various features of the invention are set forth in the following claims.

We claim:

1. A method comprising, providing a stimulation electrode assembly, comprising an elongated lead sized and configured to be implanted in adipose tissue, the lead including an electrically conductive portion to apply electrical stimulation to nerve tissue innervating the adipose tissue, and at least one expandable anchoring structure deployable from the lead to engage adipose tissue and resist dislodgment and/or migration of the electrically conductive portion within adipose tissue, selecting within the adipose tissue an adipose tissue region at or near a pubic symphysis innervated by a nerve affecting urinary function, implanting the electrically conductive portion and at least one expandable anchoring structure in the selected adipose tissue region, with the expandable anchoring structure deploying and engaging adipose tissue to resist dislodgment and/or migration of the electrically conductive portion within the selected adipose tissue region, and conveying electrical stimulation waveforms through the stimulation electrode assembly to achieve selective stimulation of the nerve to affect urinary function.

2. A method according to claim 1, wherein the selected adipose tissue region is innervated by a left and/or tight branch of the dorsal genital nerve.

3. A method according to claim 1, wherein implanting the electrically conductive portion and at least one expandable anchoring structure in the selected adipose tissue region includes placing the expandable anchoring structure in a collapsed condition, implanting the electrically conductive portion and the expandable anchoring structure in the selected adipose tissue region, and expanding the anchoring structure into the adipose tissue to resist dislodgment and/or migration of the electrically conductive portion within the selected adipose tissue region.

4. A method according to claim 3, wherein the expandable anchoring structure, when in the expanded condition, assumes an open, proximal-pointing configuration that resists proximal passage of the lead through adipose tissue in response to a pulling force that is less than or equal to a threshold axial force level.

5. A method according to claim 4, wherein the open, proximal-pointing configuration yields to permit proximal passage of the lead through adipose tissue in response to a pulling force that is greater than the threshold axial force level.

6. A method according to claim 3, further including providing a sleeve having an interior bore sized and configured to create percutaneous access to adipose tissue, and wherein implanting the electrically conductive portion and at least one expandable anchoring structure in the selected adipose tissue region includes passing the electrically conductive portion and at least one expandable anchoring structure through the interior bore of the sleeve, the interior bore of the sleeve retaining the expandable anchoring structure in the collapsed condition to accommodate passage of the electrically conductive portion and the expandable anchoring structure through the interior bore into the selected adipose tissue region.

7. A method according to claim 3, wherein the expandable anchoring structure is normally biased toward the expanded condition.

8. A method according to claim 7, further including providing a sleeve having an interior bore sized and configured to create percutaneous access to adipose tissue, wherein implanting the electrically conductive portion and at least one expandable anchoring structure in the selected adipose tissue region includes passing the electrically conductive portion and at least one expandable anchoring structure through the interior bore of the sleeve, the interior bore of the sleeve retaining the expandable anchoring structure in the collapsed condition to accommodate passing of the electrically conductive portion and the expandable anchoring structure through the interior bore into the selected adipose tissue region, and wherein upon passing the electrically conductive portion and the expandable anchoring structure into the adipose tissue region, the expandable anchoring structure returns toward the normally biased expanded condition.

9. A method according to claim 1, wherein the expandable anchoring structure comprises an array of circumferentially spaced-apart, radiating tines, and wherein implanting the electrically conductive portion and the expandable anchoring structure in the selected adipose tissue region includes placing the array of circumferentially spaced-apart, radiating tines in a collapsed condition, implanting the electrically conductive portion and the array of circumferentially spaced-apart, radiating tines in the selected adipose tissue region, and expanding the array of circumferentially spaced-apart, radiating tines into the adipose tissue to resist dislodgment and/or migration of the electrically conductive portion within the selected adipose tissue region.

10. A method according to claim 9, wherein the array of circumferentially spaced-apart, radiating tines forms an open structure that enlarges in diameter from distal to proximal to resist proximal passage of the lead through the adipose tissue region.

11. A method according to claim 1, wherein the stimulation electrode assembly comprising at least two expandable anchoring structures, and wherein implanting the electrically conductive portion and at least two expandable anchoring structures in the selected adipose tissue region includes placing the expandable anchoring structures in a collapsed condition, implanting the electrically conductive portion and the expandable anchoring structures in the selected adipose tissue region, and expanding the anchoring structures into the adipose tissue to resist dislodgment and/or migration of the electrically conductive portion within the selected adipose tissue region.

12. A method according to claim 1, wherein the lead includes a distal section, and wherein the electrically conductive portion is at or near the distal section, and wherein the expandable anchoring structure is proximal to the electrically conductive portion.

13. A method according to claim 1, wherein the expandable anchoring structure comprises a polymer material.

14. A method according to claim 1, wherein the urinary function is urinary urge incontinence.

15. A method according to claim 1, wherein the urinary function is stress incontinence.

16. A method according to claim 1, wherein the urinary function is mixed urinary urge incontinence and stress incontinence.

17. A method according to claim 1,
further including providing an implantable pulse generator sized and configured to be positioned subcutaneous to a tissue surface in an anterior pelvic region remote from the at least one electrically conductive portion,
implanting the implantable pulse generator in an anterior pelvic region remote from the at least one electrically conductive surface,
coupling the implantable pulse generator to the stimulation electrode assembly, and
wherein conveying electrical stimulation waveforms includes operating the implantable pulse generator to convey electrical stimulation waveforms through the stimulation electrode assembly to achieve selective stimulation of the nerve to affect urinary function.

18. A method according to claim 17,
further including programming and/or interrogating the implantable pulse generator using transcutaneous communication circuitry.

19. A method according to claim 1,
further including providing an external pulse generator sized and configured to convey electrical stimulation waveforms through the stimulation electrode assembly,
coupling the external pulse generator to the stimulation electrode assembly, and
wherein conveying electrical stimulation waveforms includes operating the external pulse generator to convey electrical stimulation waveforms through the stimulation electrode assembly to achieve selective stimulation of the nerve to affect urinary function.

20. A method according to claim 19,
further including providing an implantable pulse generator sized and configured to be positioned subcutaneous to a tissue surface in an anterior pelvic region remote from the at least one electrically conductive portion,
uncoupling the stimulation electrode assembly from the external pulse generator and coupling the implantable pulse generator to the stimulation electrode assembly,
implanting the pulse generator m an anterior pelvic region remote from the at least one electrically conductive portion, and
wherein conveying electrical stimulation waveforms includes operating the implantable pulse generator to convey electrical stimulation waveforms through the stimulation electrode assembly to achieve selective stimulation of the nerve to affect urinary function.

* * * * *